US005496927A

United States Patent [19]

Kolb et al.

[11] Patent Number: 5,496,927

[45] Date of Patent: Mar. 5, 1996

[54] PEPTIDASE INHIBITORS

[75] Inventors: H. Michael Kolb, Cincinnati; Joseph P. Burkhart, West Chester, both of Ohio; Michel J. Jung, Pfaffenhoffen, France; Fritz E. Gerhart, deceased, late of Kehl Leutesheim, Germany, by Jutta Gerhart, legal representative; Eugene L. Giroux, Cincinnati, Ohio; Bernhard Neises, Offenburg-Griesheim, Germany; Daniel G. Schirlin, Lampertheim, France

[73] Assignee: Merrell Pharmaceuticals Inc., Cincinnati, Ohio

[21] Appl. No.: 248,847

[22] Filed: May 25, 1994

Related U.S. Application Data

[63] Continuation of Ser. No. 102,522, Aug. 4, 1993, abandoned, which is a continuation of Ser. No. 980,141, Nov. 23, 1992, abandoned, which is a continuation of Ser. No. 540,033, Jun. 19, 1990, abandoned, which is a continuation-in-part of Ser. No. 372,162, Jun. 27, 1989, abandoned, which is a continuation of Ser. No. 267,758, Nov. 1, 1988, abandoned, which is a continuation of Ser. No. 874,721, Jun. 16, 1986, abandoned, which is a continuation-in-part of Ser. No. 697,987, Feb. 4, 1985, abandoned.

[51] Int. Cl.[6] .............................. C07K 5/00; C07K 7/00; C07K 17/00; A61K 38/00

[52] U.S. Cl. ......................... 530/328; 530/329; 530/330; 530/331; 562/575; 562/560; 562/444; 562/445

[58] Field of Search .............. 514/16–19; 530/328–331; 562/525, 560, 445, 444

[56] References Cited

U.S. PATENT DOCUMENTS 4,277,395 7/1981 Bey et al. .
4,518,528 5/1985 Rasnick .

FOREIGN PATENT DOCUMENTS 0005658 11/1979 European Pat. Off. .
0130679 1/1985 European Pat. Off. .
0189305 7/1986 European Pat. Off. .
0195212 9/1986 European Pat. Off. .
0204571 12/1986 European Pat. Off. .
1523812 9/1978 United Kingdom .
2171103 2/1986 United Kingdom .
8605379 11/1986 WIPO .
8607479 11/1986 WIPO .

OTHER PUBLICATIONS

Gelb et al., "Fluoro Ketone Inhibitors of Hydrolytic Enzymes," Biochemistry 24, No. 8, 1813–1817, (1985).

Chemical Abstracts, vol. 75, 77254 (1971) abstracting Parr, et al., Tetrahedron Lett. 28, 2633–6 (1971).

Powers, J. C., et al., "Specificity of Porcine Pancreatic Elastase, Human Leukocyte Elastase and Cathepsin G," Biochimica et Biophysica Acta 485, 156–166 (1977).

Imperiali, B., et al., "Inhibition of Serine Proteases by Peptidyl Fluoromethyl Ketones," Biochemistry 25, Imperiali et al., 3760–7 (1986).

Chemical Abstracts vol. 92, 175119 (1980).

Hori, H., et al., "Inhibition of Human Leukocyte Elastase, Porcine Pancreatic Elastase and Cathepsin G by Peptide Ketones," Enzyme Inhibitors, Proceedings of the Ninth American Peptide Symposium pp. 819–822 (1985).

Thaisrivongs, S., et al., "Diflourostatine–and Difluorostatone–Containing Peptides as Potent and Specific Renin Inhibitors," J. of Med. Chem., vol. 28, No. 11, 1553–5 (1985).

Chemical Abstracts, vol. 96, No. 176795j, p. 315, (1982) abstracting Rich, D. H., et al., Biochem. Biophys. Res. Commun., 104(3), 1127–33 (1982).

Peet, N. P., et al, "Synthesis of Peptidyl Fluoromethyl Ketones and Peptidyl α–Keto Esters as Inhibitors of Porcine Pancreatic Elastase, Human Neutrophil Elastase, and Rat and Human Neutrophil Cathepsin G", *J. Med. Chem. 33,* pp. 34–407, (1990).

Angelastro M. R., et al, "Synthesis of a Peptidyl 2,2–Difluoro–3–Aminopropionate", *Bioorganic & Medicinal Chemistry Letters,* vol. 2, No. 10, pp. 1235–1238, (1992).

Angelastro M. R., et al., "α–Diketone and α–Keto Ester Derivatives of N–Protected Amin Acids and Peptides as Novel Inhibitors of Cysteine and Serine Proteinases" *J. Med. Chem.* 33, pp. 11–13, (1990).

H. Hitoshi et al., "Inhibition of Human Leukocyte Elastase, Porcine Pancreatic Elastase and Cathepsin G by Peptide Ketones", *Enzyme Inhibitors,* pp. 819–822 (no date available).

*Journal of Medicinal Chemistry,* vol. 28, No. 11 (Nov. 1985) pp. 1553–1555.

M. H. Gelb et al., *Biochemistry,* vol. 24, No. 8, Apr. 9, 1985, pp. 1813–1817.

Thaisrivongs, S. et al., *Journal of Medicinal Chemistry,* vol. 28, No. 11 (Nov. 1985) pp. 1553–1555.

*Primary Examiner*—Jill Warden
*Assistant Examiner*—Sheela J. Huff
*Attorney, Agent, or Firm*—William R. Boudreaux

[57] ABSTRACT

This invention relates to analogs of peptidase substrates in which the amide group containing the scissile amide bond of the substrate peptide has been replaced by an activated electrophilic ketone moiety. These analogs of the peptidase substrates provide specific enzyme inhibitors for a variety of proteases, the inhibition of which will have useful physiological consequences in a variety of disease states.

7 Claims, No Drawings

PEPTIDASE INHIBITORS

CROSS-REFERENCE TO RELATED APPLICATION

This is a continuation, of application Ser. No. 08/102,522, filed Aug. 4, 1993 now abandoned, which is a continuation of application Ser. No. 07/980,141 filed Nov. 23, 1992 now abandoned, which is a continuation of application Ser. No. 07/540,033 filed Jun. 19, 1990 now abandoned, which is a continuation in part of application Ser. No. 372,162 filed Jun. 27, 1989 now abandoned, which is a continuation of application Ser. No. 267,758 filed Nov. 1, 1988 now abandoned which is a continuation of application Ser. No. 874,721 filed Jun. 16, 1986 now abandoned which is a continuation in part of application Ser. No. 697,987 filed Feb. 4, 1984 now abandoned which is herein incorporated by reference.

This invention relates to protease enzyme inhibitors useful for a variety of physiological end-use applications.

In its broad aspects, this invention relates to analogs of peptidase substrates in which the amide group containing the scissile amide bond of the substratepeptide has been replaced by an activated electrophilic ketone moiety such as fluoromethylene ketone or -keto carboxyl derivatives. These analogs of the peptidase substrates provide specific enzyme inhibitors for avariety of proteases, the inhibition of which will have useful physiological consequences in a variety of disease states. In its more specific aspects, this invention relates to activated electrophilic ketone derivatives of certain peptidase substrates which are useful in inhibitingserine-, thiol-, carboxylic acid- and metallo- dependent protease enzymes, the inhibition of which will have useful physiological consequences in a variety of disease states.

Still more specifically, this invention relates to activated electrophilic ketone derivatives of peptidase substrates which fall within the following generic groupings characterized according to their active site dependencies. Such generic groupings are:

I. Serine Dependent Enzymes: These include such enzymes as Elastase (human leukocyte), Cathepsin G, Thrombin, Plasmin, C-1 Esterase, C-3 Convertase, Urokinase, Plasminogen Activator, Acrosin, β-Lactamase, D-Alanine-D-Alanine Carboxypeptidase, Chymotrypsin, Trypsin and Kallikreins.

II. Thiol Dependent Enzymes: Cathepsin B.

III. Carboxylic Acid Dependent Enzymes: These include such specific enzymes as Renin, Pepsin and Cathepsin D.

IV. Metallo Dependent Enzymes: These include Angiotensin Converting Enzyme, Enkephalinase, Pseudomonas Elastase and Leucine Aminopeptidase.

The contemplated peptidase inhibitors of the foregoing enzymes are selected from the generic formula

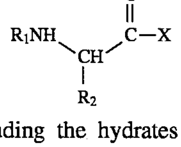

I including the hydrates thereof, and the parhmaceutically acceptable salts thereof wherein X embraces subgroups X1 and X2, wherein $X_1$ is $-CF_2H$, $-CF_3$, $CO_2R_3$ or $-CONHR_3$, and $X_2$ is 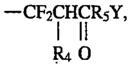, 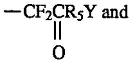 and 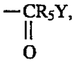, $R_2$ is the side chain of the α-amino acid responsible for directing the inhibitor to the active site of the enzyme, $R_1$ is H, an amino protecting group selected from Group K, an α-amino acid or a peptide having up to 4 α-amino acids sequenced in their $P_2$ to $P_5$ position, the terminal amine of said α-amino acid or peptide optionally bearing a protecting group selected from Group K, $R_3$ may be H, $C_{1-4}$ straight or branched alkyl, phenyl, cyclohexyl, cyclohexylmethyl or benzyl, $R_4$ is a side chain of an α-amino acid for that peptidase substrate analog, $R_5$ is an α-amino acid or peptide having up to 3 α-amino acids sequenced in their $P'_2$ to $P'_4$ positions, or is deleted, (sometimes herein stated "or is zero", and Y is $NHR_3$ or $OR_3$, with the proviso that when R2 is a side chain of an α-amino acid of Group E and the $R_1$ moiety bears a member of Group D in its $P_2$ position, then X is other than $CF_3$.

Unless otherwise stated the α-amino acids of these peptidase substrates are preferably in their L-configuration.

Before further defining and/or illustrating the scope of the peptidase substrate inhibitors embraced by formula I, it may be convenient to state some of the more basic concepts related to peptides. For example, except for proline, all of the α-amino acids found in proteins have, as a common denominator, a free carboxyl group and a free unsubstituted amino group on the α-carbon atom (in proline, since proline's α-amino group is substituted it is really an α-imino acid, but for convenience, it will also be spoken of as an α-amino group). Additionally each α-amino acid has a characteristic "R-group", the R-group being the side-chain, or residue, attached to the α-carbon atom of the α-amino acid. For example, the R-group side chain for glycine is hydrogen, for alanine it is methyl, for valine it would be isopropyl. (Thus, throughout this specification the $R_2$ or $R_4$ moiety is the side-chain for each indicated α-amino acid). For the specific side chains of the α-amino acids reference to A. L. Lehninger's text on Biochemistry (see particularly Chapter 4) would be helpful.

As a further convenience for defining the scope of the compounds embraced by the generic concept of Formula I, as well as the sub-generic concepts relating to each of the individual enzymes involved in this invention, various α-amino acids have been classified into a variety of groups which impart similar functional characteristics for each of the specific enzymes to be inhibited by the pepti-dase substrates of Formula I. These groups are set forth in Table II and the recognized abbreviations for the α-amino acid blocks are set forth in Table I.

TABLE I

| Amino Acid | Symbol |
|---|---|
| Alanine | Ala |
| Arginine | Arg |
| Asparagine | Asn |
| Aspartic acid | Asp |
| Asn + Asp | Asx |
| Cysteine | Cys |
| Glutamine | Gln |
| Glutamic acid | Glu |
| Gln + Glu | Glx |
| Glycine | Gly |
| Histidine | His |
| Isoleucine | Ile |
| Leucine | Leu |
| Lysine | Lys |
| Methionine | Met |
| Phenylalanine | Phe |
| Proline | Pro |
| Serine | Ser |

TABLE I-continued

| Amino Acid | Symbol |
|---|---|
| Threonine | Thr |
| Tryptophan | Trp |
| Valine | Val |
| Norvaline | n-Val |
| n-Leucine | n-Leu |
| 1-Naphthylalanine | Nal (1) |
| 2-Indolinecarboxylic Acid | Ind |
| Sarcosin | Sar |

TABLE II

Group

A: Lys and Arg

B: Glu, Asp

C: Ser, Thr, Gln, Asn, Cys, His

D: Pro, Ind

E: Ala, Leu, Ile, Val, n-Val, Met, n-Leu and N-methyl derivatives

F: Phe, Tyr, Trp, Nal (1), and N-methyl derivatives

G: Gly, Sar

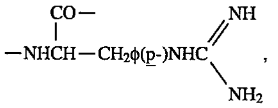

(J-1)

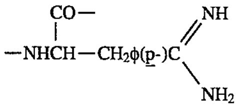

(J-2)

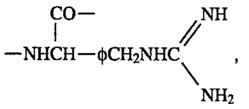

(J-3)

and

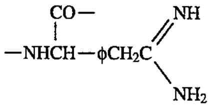

(J-4)

with ϕ representing phenyl

K: Acetyl (Ac) Acetyl (Ac) Succinyl (Suc), Benzoyl (Bz) t-Butyloxycarbonyl (Boc), Carbobenzoxy (CBZ), Tosyl (Ts), Dansyl (DNS), Isovaleryl (Iva), Methoxysuccinyl (MeOSuc), 1-Adamantanesulphonyl ($AdSO_2$), 1-Adamantaneacetyl (AcAc), 2-Carboxybenzoyl (2-CBZ) and such other terminal equivalent thereto.

In light of the foregoing, the defined compounds of formula I may also be stated as being:

An activated electrophilic ketone-bearing peptidase inhibitor of the formula

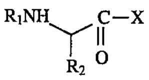

the hydrates thereof, and the pharmaceutically acceptable salts thereof wherein $R_1$ is H, an amino protecting group selected from Group K, an α-amino acid or a peptide having up to 4 α-amino acids sequenced in their $P_2$ to $P_5$ position, the terminal amine of said α-amino acid or peptide optionally bearing a protecting group selected from Group K, $R_2$ is the side chain of an α-amino acid, X is $X_1$ or $X_2$ wherein $X_1$ is $CF_3$, $CF_2H$, $CO_2R_3$ or $-CONHR_3$, and $X_1$ is 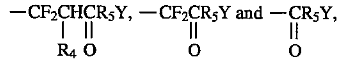

$R_3$ is hydrogen, $C_{1-4}$ straight or branched alkyl, phenyl, benzyl, cyclohexyl or cyclohexylmethyl, $R_4$ is the side chain of an α-amino acid, $R_5$ is an α-amino acid or a peptide having up to 3 α-amino acids sequenced in their $P'_2$ to $P'_4$ positions, or is deleted, Y is $-NHR_3$ or $-OR_3$ with the proviso that when $R_2$ is a side chain of an α-amino acid of Group E and the $R_1$ moiety bears a member of Group D in its $P_2$ position, then X is other than $CF_3$, wherein the said α-amino acid and peptide moieties are building blocks selected from Groups, A, B, C, D, E, F, G, J and K is a terminal amino protecting group, members of these groups being Group A: Lys and Arg, B: Glu and Asp, C: Ser, Thr, Gln, Asn, Cys and His, D: Pro, Ind, E: Ala, Leu, Ile, Val, n-Val, Met and n-Leu, and N-methyl derivatives, F: Phe, Tyr and Trp, Nal (1), and N-methyl derivatives, G: Gly, Sar,

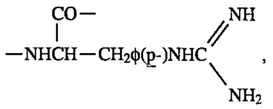

(J-1)

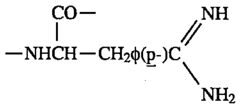

(J-2)

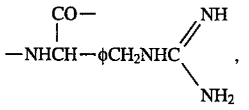

(J-3)

and

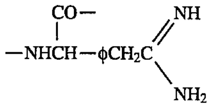

(J-4)

with ϕ representing phenyl.

K: Acetyl (Ac) Succinyl (Suc), Benzoyl (Bz) t-Butyloxycarbonyl (Boc), Carbobenzoxy (CBZ), Tosyl (Ts), Dansyl (DNS), Isovaleryl (Iva), Methoxysuccinyl (MeOSuc), 1-Adamantanesulphonyl ($AdSO_2$), 1-Adamantaneacetyl (AdAc), 2-Carboxybenzoyl (2-CBz) and such other terminal amino protecting groups which are functionally equivalent thereto.

To illustrate those compounds which are useful as enzyme inhibitors for human leukocyte elastase, and to serve as a medium of instruction for a better understanding of the scope of compounds embraced within the generic formula I, (and its sub-generic formulae for each of the involved enzymes herein disclosed) the following formula (Ia) represents the subgeneric class defining those compounds within the scope of inhibitors of human leukocyte elastase:

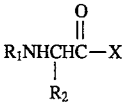

(Ia)

wherein $R_2$ is the side chain of the depicted enzyme-directing α-amino acid (P1), $R_1$ is as previously defined (Comprised of $P_2$-$P_n$ blocks), and X is the moiety conferring the electrophilic character to its adjacent carbonyl consisting of either $X_1$ or $X_2$ as previously defined generically in formula I.

Still for instructional purposes, the structural formula for the most preferred human leukocyte elastase inhibitor is

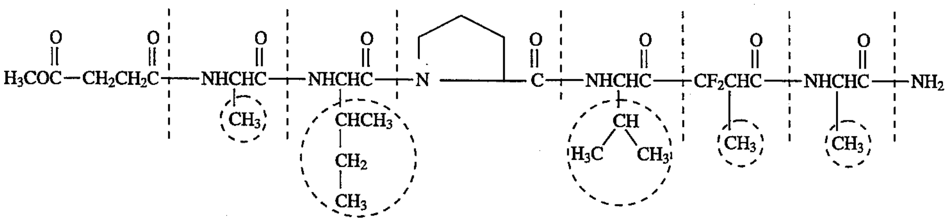

II

P5 P4 P3 P2 P1 P1' P2' P3' the vertical dotted lines setting off each moiety constituting the specific arrangement for that particular peptidase inhibitor. Except for proline and 2-indoline carboxylic acid the moieties encircled within the dotted lines represent the side chains of the α-amino acids (see pages 69–71 of the above cited Lehninger's text) or 1-naphthylmethyl.

Still another way of representing the foregoing substrate is by the formula

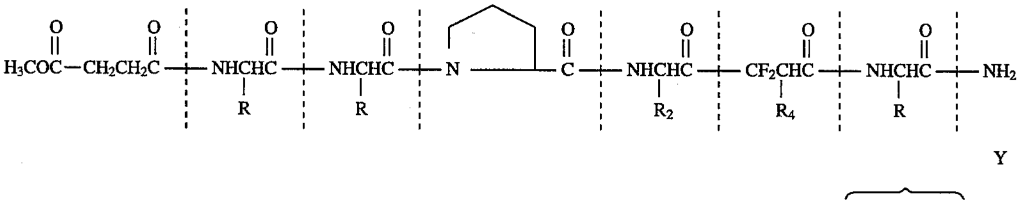

III

P5 P4 P3 P2 P1 P1' P2' P3' with R, $R_2$, $R_4$ being the side chains of the particular α-amino acid, the amino acid of $P'_2$ ($P_2$ primed) being the $R_5$, if any, of $X_2$ and the terminal $P'_3$ being a specific of the Y radical of $X_2$, $P_5$ being the terminal moiety sometimes referred to generically as ($P_n$) and $P_2$-$P_3$-$P_4$ being the remaining α-amino acids of that $R_1$ moiety.

Still another, and the most convenient method for simply conveying the structure involved is the formula

IV

| MeOSuc | —Ala | —Ile | —Pro | —Val | —X |
|---|---|---|---|---|---|
| $P_5$ | $P_4$ | $P_3$ | $P_2$ | $P_1$ | $P_1'$-$P_2'$ Y |

wherein X consists of $P'_1$-$P'_2$Y when representative of

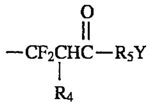

wherein for the illustrations above, $P'_1$ bears the $-CH_3$ side chain for $R_4$ and $P'_2$ bears the $R_5$ amino acid bearing the $-CH_3$ side chain and Y is $NH_2$, and $P_1$-$P_5$ are shorthand designations for the depicted $P_1$-$P_5$ moieties of the above structures II and III.

To expand on structure IV and (Ia) as it encompasses the scope of the other X moieties attached to the same $P_1$-$P_5$ moieties, the following seven structures are shown:

(a) MeOSuc-Ala-Ile-Pro-Val-$CF_2H$ (i.e., $X_1$ is $-CF_2H$);

(b) MeOSuc-Ala-Ile-Pro-Val-$CF_3$ (i.e., $X_1$ is $-CF_3$);

(c) MeOSuc-Ala-Ile-Pro-Val-COOH (i.e., $X_1$ is $-CO_2R_3$ with $R_3$ being H);

(d) MeOSuc-Ala-Ile-Pro-Val-$CONH_2$ (i.e., $X_1$ is $-CONHR_3$ with $R_3$ being H).

(e)

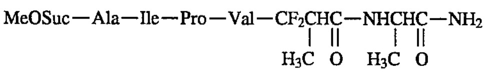

(i.e., $X_2$ is

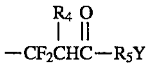

with $R_4$ being the side chain of alanine, $R'_5$ and being the side chain of alanine and Y is $NH_2$;

(f)

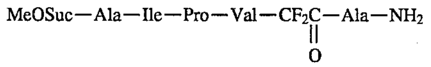

(i.e., $X_2$ is

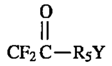

with $R_5$ being as defined in (e) above, and Y is $NH_2$; and (g)

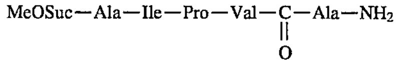

(i.e., $X_2$ is

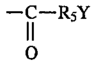

wherein $R_5$ is as defined in (e) above and Y is $NH_2$.

It is also convenient when defining the substrate compounds according to the foregoing formula IV convention designation to define the

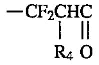

moiety of $X_2$ as [$CF_2$-α-amino acid] wherein the name of the α-amino acid to which $R_4$ is a side chain is indicated such as, for example, this convention

becomes [$CF_2$ Ala].

This will facilitate the writing and comprehension of the so-defined structures.

In the definitions of the $R_1$ moieties of the following subgeneric formulae (i.e. Ia through Iv) it is to be understood that $P_g$ is the optional N-protecting group of the terminal α-amino acid. Thus, for example, if the $R_1$ definition is $P_2P_3P_4P_g$ and $P_3$ and/or $P_4$ are deleted, then the optional Group K protecting group would be on the terminal amine of the $P_2$-α-amino acid.

Utilizing the foregoing illustrations those compounds of formula I which are useful as inhibitors for human leukocyte elastase are represented by the formula

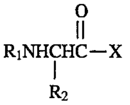

(Ia)

wherein $R_2$ is the side chain of the α-amino acids of Groups E and G, with nor-valine and valine being preferred, with the proviso that when $R_2$ is a side chain of an α-amino acid of Group E and the $R_1$ moiety bears a member of Group D in its $P_2$ position, then X is other than $CF_3$.

$R_1$ is -$P_2P_3P_4P_g$ with $P_2$ being selected from Groups D, E and F, with proline being preferred, $P_3$ is selected from Groups D or E, with isoleucine being preferred, $P_4$ is selected from Groups E or zero with alanine being preferred (when $P_n$ is zero then that particular moiety does not appear in the structure, i.e. it is deleted, $P_g$ is selected from Group K with methoxysuccinyl being preferred, X is any of the $X_1$ or $X_2$ moieties defined for formula I with $R_5$ being an α-amino acid of Groups E and G with alanine being preferred and Y is $NH_2$, and $R_4$ is a side chain of an amino acid of Groups E and G with the side chain of alanine preferred.

Human leukocyte elastase is released by polymorphonuclear leukocytes at sites of inflammation and thus is a contributing cause for a number of disease states. Thus the peptidase substrates of Formula (Ia) have an anti-inflammatory effect useful in the treatment of gout, rheumatoid arthritis and other inflammatory diseases, and in the treatment of emphysema. In their end-use application the enzyme inhibitory properties of the compounds of (Ia) are readily ascertained by standard biochemical technique well known in the art. Potential dose range for their end-use application will of course depend upon the nature and severity of the disease state as determined by the attending diagnostician with the range of 0.01 to 10 mg/kg body per day being useful for the aforementioned disease states. The preferred compounds for this enzyme are:

MeOSuc-Ala-Ile-Pro-Val[$CF_2$-Ala]Ala-$NH_2$,
MeOSuc-Ala-Ile-Pro-Val-$CF_3$,
MeOSuc-Ala-Ile-Pro-Val-$CO_2$Me,
MeOSuc-Ala-Ile-Pro-Val-$CF_2$COOEt,
MeOSuc-Ala-Ile-Pro-Val-$CHF_2$,
MeOSuc-Ala-Ala-Pro-Val-$CO_2$Me,
MeOSuc-Ala-Ala-Pro-Val-[$CF_2$-Ala]Ala-$NH_2$,
MeOSuc-Ala-Ala-Pro-Val-$CF_3$,
[αN-($AdSO_2$)]-[N-(2-CBz)]-Lys-Pro-Val-[$CF_2$Ala]Ala-$NH_2$,
[αN-($AdSO_2$)]-[N-(2-CBz)]-Lys-Pro-Val-$CHF_2$,
[αN-($AdSO_2$)]-[N-(2-CBz)]-Lys-Pro-Val-$CO_2$Me,
MeOSuc-Ala-Ile-Pro-Val-$CO_2$Me, and
MeOSuc-Ala-Ile-Pro-Val-$CO_2$H.

Those compounds of Formula I which are useful as inhibitors of Cathepsin G are represented by the structural formula

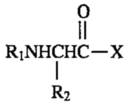

(Ib)

wherein $X_1$, $X_2$, $R_3$, $R_4$, $R_5$ and Y are as defined for human leukocyte elastase (Formula Ia), $R_1$ is $P_2$-$P_3$-$P_4$-$P_g$ with $P_2$ being selected from Groups D, E, G or K with proline or benzoyl being preferred, $P_3$ is selected from Groups E or G with alanine being preferred, $P_4$ is selected from Groups E, G or is deleted with alanine being preferred, $P_g$ is selected from Group K with succinyl being preferred, $R_2$ is a side chain of an amino acid of Groups E and F but preferably is the Phe side chain, with the proviso that when $R_2$ is a side chain of an amino acid of Group E and the $R_1$ moiety bears a member of Group D in its $P_2$ position, then X is other than $CF_3$.

The end-use application of the compounds (Ib) inhibiting Cathepsin G is the same as for human leukocyte elastase inhibitors, including arthritis, gout and emphysema, but also embracing the treatment of glomerulonephritis and lung infestations caused by infections in the lung. For their end-use application, the potency and other biochemical parameters of the enzyme inhibiting characteristics of the compounds of (Ib) is readily ascertained by standard biochemical techniques well known in the art. Actual dose ranges for their specific end-use application will, of course, depend upon the nature and severity of the disease state of the patient or animal to be treated as determined by the attending diagnostician. It is to be expected that the general end-use application dose range will be about 0.01 to 10 mg per kg per day for an effective therapeutic effect. Preferred compounds of formula Ib are:

Suc-Ala-Ala-Pro-Phe-$X_1$, and specifically
Suc-Ala-Ala-Pro-Phe-$CF_3$,
Suc-Ala-Ala-Pro-Phe-COOH,
Suc-Ala-Ala-Pro-Phe-COOMe,
Suc-Ala-Ala-Pro-Phe-$CF_2H$,
Suc-Ala-Ala-Pro-Phe[$CF_2$Ala]OH, and
Suc-Ala-Ala-Pro-Phe-$CF_2$-COOEt.

Those compounds of Formula I which are useful as inhibitors of thrombin are represented by the formula

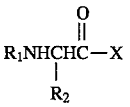

(Ic)

wherein X is $X_1$ or $X_2$ as defined in formula I with Y being OH,

- $R_5$ is preferably glycine or is a member of Group E or D or is zero,
- $R_4$ is the side chain of an amino acid selected from Group C or G but preferably is the glycine or serine side chain,
- $R_2$ is preferably the arginine side chain but may also be a side chain of an amino acid selected from Groups A and J,
- $R_1$ is (a)-$P_2$-$P_3$, (b)-$P_g$ or (c)-$P_2$-$P_3$-$P_4$-$P_g$ with
  - (a) $P_2$ is selected from Groups D, E or F, preferably proline, $P_3$ is selected from Group F, each $P_3$ being in the D—configuration preferably D-Phe,
  - (b) $P_g$ is selected from Group K and is preferably dansyl or tosyl,
  - (c) $P_2$ is selected from Group E but preferably is alanine, $P_3$ is selected from Groups C, G and E but preferably is serine, $P_4$ is selected from Groups F, G and E or is zero but preferably is Phe, Pg is an optional Group K amino protecting group.

The compounds embraced by Formula (Ic) inhibit thrombin and therefore, as in the use of heparin, the compounds may be used as the initial anticoagulant agent in thrombophlebitis and coronary thrombosis. For their end-use application, the potency and other biochemical parameters of the enzyme inhibiting characteristics of the compounds of (Ic) are readily ascertained by standard biochemical techniques well known in the art. Actual dose ranges for their specific end-use application will, of course, depend upon the nature and severity of the disease state of the patient or animal to be treated as determined by the attending diagnostician. It is to be expected that the general end-use application dose range will be about 0.01 to 10 mg per kg per day for an effective therapeutic effect. Preferred compounds are as expressed for Cathepsin G and also include:

H—(D)—Phe—Pro—Arg—$CF_3$,
H—(D)—Phe—Pro—Arg—COOH,
H—(D)—Phe—Pro—Arg—COO-n-butyl,
DNS—Arg—$CF_3$,
DNS—Arg—COOH,
DNS—Arg—COO-n-butyl,
H—Phe—Ser—Ala—$CF_3$,
H—Phe—Ser—Ala—COOH,
H—Phe—Ser—Ala—COO-n-butyl,

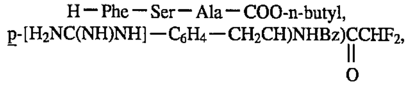

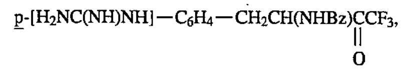

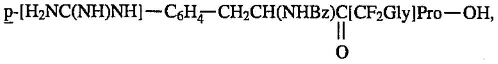

and p-[$H_2$NC(NH)NH]—$C_6H_4$—$CH_2$CH(NHBz)COOH.

The compound of Formula I which are useful as inhibitors of chymotrypsin are represented by the structural formula

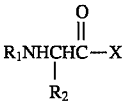

(Id)

wherein $X_1$, $X_2$, $R_3$, $R_4$, $R_5$ and Y are as defined for compounds of Ia, and $R_1$ is -$P_2$-$P_3$-$P_4$-$P_g$ with,

- $P_2$ being selected from Groups D, E, G,
- $P_3$ is selected from Groups E or G or is zero with alanine being preferred,
- $P_4$ is selected from Groups E or G or is deleted with alanine being preferred,
- $P_g$ is an optional Group K amino protecting group with succinyl and benzoyl being preferred, and
- $R_2$ is selected from a side chain of an amino acid of Groups E and F but preferably is Phe or Tyr side chains, with the proviso that when $R_2$ is a side chain of an α-amino acid of Group E and the $R_1$ moiety bears a member of Group D in its $P_2$ position, then X is other than $CF_3$.

The end-use application of the compounds (Id) inhibiting chymotrypsin is in the treatment of pancreatitis. For their end-use application, the potency and other biochemical parameters of the enzyme inhibiting characteristics of the compounds of (Id) is readily ascertained by standard biochemical techniques well known in the art. Actual dose ranges for their specific end-use application will, of course, depend upon the nature and severity of the disease state of the patient or animal to be treated as determined by the attending diagnostician. It is to be expected that the general end-use application dose range will be about 0.01 to 10 mg per kg per day for an effec-tive therapeutic effect. Preferred compounds are as expressed for Chymotrypsin and also include:

Bz-Phe-$CF_3$,
Bz-Phe-COOH,
Bz-Phe-COOMe,
Bz-Tyr-$CF_3$,
Bz-Tyr-COOH,
Bz-Tyr-COOMe,
Bz-Phe-$CHF_2$,
Bz-Phe-$CF_2$COOEt, and
Bz-Phe-[$CF_2$-Gly]Gly-OH.

The compounds of Formula I which are useful as inhibitors of trypsin are represented by the structural formula

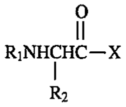
(Ie)

wherein X is $X_1$ or $X_2$ as defined in formula I with Y being OH, $R_5$ is selected from Groups G, E or D or is zero but preferably is glycine, $R_4$ is a side chain of an amino acid of Groups C or G but preferably is the glycine or serine side chain, $R_2$ is a side chain of an amino acid selected from Groups A or J but preferably is the arginine side chain, $R_1$ is selected from (a)-$P_2$-$P_3$, (b)-$P_2$ or (c)-$P_2$-$P_3$-$P_4$-$P_g$ with (a) $P_2$ is selected from Groups D, E or F but is preferably proline or alanine, $P_3$ is selected from Group F, (each being in the D configuration) but preferably is (D)-Phe, (b) $P_g$ is selected from Group K but preferably is dansyl or tosyl, (c) $P_2$ is selected from Group D or E but preferably is proline or alanine, $P_3$ is selected from Groups C, G and E but preferably is serine, $P_4$ is selected from Groups G and E or is zero but preferably is Phe. Pg of (a) and (c) are optional Group K amine protecting groups.

The end-use application of the compounds (Ie) inhibiting trypsin is in the treatment of pancreatitis. For their end-use application, the potency and other biochemical parameters of the enzyme inhibiting characteristics of the compounds of (Ie) is readily ascertained by standard biochemical techniques well known in the art. Actual dose ranges for their specific end-use application will, of course, depend upon the nature and severity of the disease state of the patient or animal to be treated as determined by the attending diagnostician. It is to be expected that the general end-use application dose range will be about 0.01 to 10 mg per kg per day for an effective therapeutic effect. The preferred compounds useful for inhibiting trypsin are the same as for the inhibitors of thrombin.

The compounds of Formula I which are useful as inhibitors of plasmin are represented by the structural formula

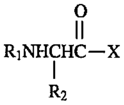
(If)

wherein X is $X_1$ or $X_2$, with $CF_3$, COOH, COOMe, and $CF_2COOEt$ being preferred, $R_1$ is -$P_2$-$P_3$-$P_g$ with $P_2$ being selected from Group F but preferably is Phe, $P_3$ is selected from Groups B or F but preferably is Glu, and $P_g$ is an optional Group K (preferably dansyl) amino protecting group, $R_2$ is a side chain of an amino acid selected from Groups A and J but preferably is the lysine side chain.

The compounds embraced by formula (If) inhibit plasmin and are therefore antiproliferative agents useful in treating excessive cell growth, particularly in the treatment of benign prostatic hypertrophy and prostatic carcinoma, and in the treatment of psoriasis. For their end-use application, the potency and other biochemical parameters of the enzyme inhibiting characteristics of the compounds of (If) is readily ascertained by standard biochemical techniques well known in the art. Actual dose ranges for their specific end-use application will, of course, depend upon the nature and severity of the disease state of the patient or animal to be treated as determined by the attending diagnostician. It is to be expected that the general end-use application dose range will be about 0.01 to 10 mg per kg per day for an effective therapeutic effect. The preferred compounds are:

DNS-Glu-Phe-Lys-$CHF_2$,
DNS-Glu-Phe-Lys-COOH,
DNS-Glu-Phe-Lys-$CF_3$,
DNS-Glu-Phe-Lys-COOMe, and
DNS-Gly-Phe-Lys-$CF_2COOEt$.

The compounds of Formula I which are useful as inhibitors of $C_1$-esterase are represented by the structural formula

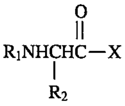
(Ig)

wherein X is $X_1$ or $X_2$ with $X_1$ being preferred particularly when $X_1$ is $CO_2R_3$ or -$CF_3$, $R_2$ is a side chain of an amino acid selected from Groups A and J but preferably is the Arg side chain, $R_1$ is -$P_2$-$P_g$ with $P_2$ being selected from Groups E, G, D, C, F, A or B with Ala being preferred, and $P_g$ is an optional Group K amino protecting group with CBZ being preferred, $R_4$ is selected from the side chains of the amino acids of Group E, and $R_5$ is selected from Group E and Y is preferably $NH_2$.

The compounds embraced by formula (Ig) inhibit $C_1$-esterase and are therefore useful in treating systemic lupus, arthritis, autoimmune hemolytic anemia and glomerulonephritiso. For their end-use application, the potency and other biochemical parameters of the enzyme inhibiting characteristics of the compounds of (Ig) is readily ascertained by standard biochemical techniques well known in the art. Actual dose ranges for their specific end-Use application will, of course, depend upon the nature and severity of the disease state of the patient or animal to be treated as determined by the attending diagnostician. It is to be expected that the general end-use application dose range will be about 0.01 to 10 mg per kg per day for an effective therapeutic effect. The preferred compounds are:

CBZ-Ala-Arg-$CF_3$,
CBZ-Ala-Arg-COOH,
CBZ-Ala-Arg-COOMe,
CBZ-Ala-(p-gua)*-Phe-$CF_2COOEt$, and
CBZ-Ala-p-gua)*-Phe[$CF_2$Ala]$NH_2$.

*gua is guanidino.

The compounds of Formula I which are useful as inhibitors of $C_3$-convertase are represented by the formula

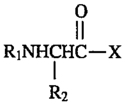
(Ih)

$R_4$ preferably being the alanine side chain, but is also a side chain of an amino acid of Group E, $R_5$ is zero and Y is $OR_3$ (i.e., $R_5Y$ is $OR_3$), $R_2$ is a side chain of an amino acid selected from Groups A or J, with the Arg side chain being preferred, $R_1$ is -$P_2$-$P_3$-$P_g$ with $P_2$ being selected from Groups E or F, with Ala being preferred, $P_3$ is selected from Groups E or F with Leu being preferred, and $P_g$ is an optional Group K amino protecting group with Bz being preferred.

The compounds embraced by formula (Ih) inhibit $C_3$-convertase and are therefore useful in treating systemic lupus, arthritis, autoimmune hemolytic anemia and glomerulonephritis. For their end-use application, the potency and other biochemical parameters of the enzyme inhibiting characteristics of the compounds of (Ih) is readily ascertained by standard biochemical techniques well known in the art. Actual dose ranges for their specific end-use application will, of course, depend upon the nature and severity of the disease state of the patient or animal to be treated as determined by the attending diagnostician. It is to be expected that the general end-use application dose range will be about 0.01 to 10 mg per kg per day for an effective therapeutic effect. The preferred compounds are:

Bz-Leu-Ala-Arg-$CF_3$,
Bz-Leu-Ala-Arg-$CHF_2$,
Bz-Leu-Ala-Arg-$CF_2$-COO-$CH_2\phi$,
Bz-Leu-Ala-Arg[$CF_2$-Ala]$OCH_2\phi$, and
Bz-Leu-Ala-Arg-$COOCH_2\phi$.

The compounds of formula I which are useful as inhibitors of Urokinase are represented by the formula

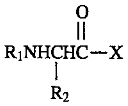
(Ii)

wherein X is $X_1$ or $X_2$ with $X_1$ being preferred and $CO_2R_3$ and -$CF_3$ being most preferred, $R_4$ is a side chain of an amino acid of Group E, $R_5$ is selected from Group E, and Y is $NH_2$, $R_1$ is -$P_2$-$P_3$ with $P_2$ being selected from Groups E and G with Ala and Gly being preferred, and $P_3$ is selected from Group B with Glu being preferred, $R_2$ is a side chain of an amino acid selected from Groups A and J with the side chain of Arg being preferred. Preferred Urokinase inhibitors are:

H-Glu-Gly-Arg-$CF_2H$,
H-Glu-Gly-Arg-$CF_3$,
H-Glu-Gly-Arg-COOH,
H-Glu-Gly-Arg-$CONH_2$,
H-Glu-Gly-(p-gua)*Phe-[$CF_2$Ala]-Ala-$NH_2$, and
H-Gly-Gly(p-gua)*Phe-$CF_2CONH_2$,

*(p-gua) being para-guanidino

The compounds of formula (Ii) inhibit urokinase and therefore are useful in treating excessive cell growth disease states. As such the compounds are useful in the treatment of benign prostatic hypertrophy and prostatic carcinoma, the treatment of psoriasis, and in their use as abortifacients. For their end-use application, the potency and other biochemical parameters of the enzyme inhibiting characteristics of the compounds of (Ii) are readily ascertained by standard biochemical techniques well known in the art. Actual dose ranges for their specific end-use application will, of course, depend upon the nature and severity of the disease state of the patient or animal to be treated as determined by the attending diagnostician. It is to be expected that the general end-use application dose range will be about 0.01 to 10 mg per kg per day for an effective therapeutic effect.

The compounds of Formula I which are useful as inhibitors of plasminogen activator are represented by the structural formula

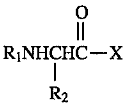
(Ij)

wherein X is $X_1$ or $X_2$ with $X_1$ being preferred and -$CF_3$, COOH and COOMe being most preferred, $R_4$ is a side chain of an amino acid of Group E, R5 is selected from Group E, Y is $NH_2$ when X is $X_2$, $R_1$ is -$P_2$-$P_3$-$P_g$ wherein $P_2$ is Gly, $P_3$ is selected from Group B with Glu being preferred, and $P_g$ is a Group K amino protecting group preferably dansyl, and $R_2$ is a side chain of an amino acid selected from Groups A and J with Arg being preferred. Preferred compounds are:

DNS-Glu-Gly-Arg-COOMe,
DNS-Glu-Gly-Arg-$CF_3$,
DNS-Glu-Gly-Arg-COOH,
DNS-Glu-Gly-(p-gua)Phe-$CHF_2$,
DNS-Glu-Glu-(p-gua)Phe[$CF_2$Ala]Ala$NH_2$, and
DNS-Glu-Gly-(p-gua)Phe$CF_2$COOEt.

The compounds of the Formula (Ij) inhibit plasminogen activator and therefore are useful in treating excessive cell growth disease states such, for example, being useful in the treatment of benign prostatic hypertrophy and prostatic carcinoma, in the treatment of psoriasis and in their use as abortifacients. For their end-use application, the potency and other biochemical parameters of the enzyme inhibiting characteristics of the compounds of (Ij) is readily ascertained by standard biochemical techniques well known in the art. Actual dose ranges for their specific end-use application will, of course, depend upon the nature and severity of the disease state of the patient or animal to be treated as determined by the attending diagnostician. It is to be expected that the general end-use application dose range will be about 0.01 to 10 mg per kg per day for an effective therapeutic effect.

The compounds of Formula I which are useful as inhibitors of acrosin are represented by the structural formula

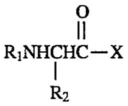
(Ik)

wherein X is $X_1$ or $X_2$, with $X_1$ being preferred, especially when $X_1$ is -$CF_3$, $CHF_2$, COOH or COOMe. When X is $X_2$, $R_4$ is a side chain of an amino acid of Group E, $R_5$ is Group E, or is deleted and Y is $NH_2$, $R_1$ is -$P_2$-$P_3$-$P_g$ with $P_2$ being selected from Group E with Leu being preferred, $P_3$ is selected from Group E with Leu being preferred, $P_g$ is an optional Group K amino protecting group with Boc being preferred, and $R_2$ is a side chain of an amino acid selected from Groups A and J with the side chain of Arg being preferred. Preferred compounds are:

Boc-Leu-Leu-Arg-$CF_2H$,
Boc-Leu-Leu-Arg-$CF_3$,
Boc-Leu-Leu-Arg-COOH,
Boc-Leu-Leu-(p-gua)Phe-[$CF_2$Ala]Ala$NH_2$, and
Boc-Leu-Leu-(p-gua)Phe$CF_2CONH_2$.

The compounds of formula (Ik) are acrosin inhibitors and therefore are useful as anti-fertility agents in that they possess the characteristics of preventing sperm from penetrating an otherwise fertilizable egg. For their end-use application, the potency and other biochemical parameters of the enzyme inhibiting characteristics of the compounds of (Ik) are readily ascertained by standard biochemical techniques well know in the art. Actual dose ranges for their specific end-use application will, of course, depend upon the state of the patient or animal to be treated as determined by the attending diagnostician. It is to be expected that the general end-use application dose range will be about 0.01 to 10 mg per kg per day for an effective therapeutic effect.

The compounds of Formula I which are useful as inhibitors of β-lactamase are represented by the structural formula

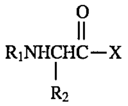

(II)

with the proviso that the depicted carbonyl moiety (attached to X) may exist in its chemically reduced form, i.e.,

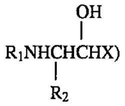

with the reduced form being preferred, wherein X is $X_1$ or $X_2$ with $-CF_3$, COOH and COOMe being most preferred, and $R_5$ is deleted when X is $X_2$, $R_1$ is $P_g$, $P_g$ being selected from Group K with $COCH_2\phi$ and Bz being preferred, $R_2$ is a side chain of an amino acid selected from Group E, G and C with the side chain of glycine being preferred. The preferred compounds are:

$\phi CH_2COHNCH_2COCF_3$,
$\phi CH_2COHNCH_2COCOOH$,
$\phi CH_2COHNCH_2COCOOMe$,
$\phi CH_2COHNCH_2CHOHCF_3$,
$\phi CH_2COHNCH_2CHOHCOOH$,
$\phi CH_2COHNCH_2CHOHCOOMe$,
$\phi CH_2COHNCH_2COCHF_2$, and
$\phi CH_2COHNCH_2CHOHCF_2COOEt$.

The compounds embraced by formula (I1) inhibit β-Lactamase and therefore are useful in the potentiation of anti-bacterial agents, particularly the β-lactam anti-bacterials. For their end-use application, the potency and other biochemical parameters of the enzyme inhibiting characteristics of the compounds of (I1) are readily ascertained by standard biochemical techniques well known in the art. Actual dose ranges for their Specific end-use application will, of course, depend upon the nature and severity of the disease state of the patient or animal to be treated as determined by the attending diagnostician. It is to be expected that the general end-use application dose range will be about 0.01 to 10 mg per kg per day for an effective therapeutic effect.

The compounds of Formula I which are useful as inhibitors of D-Ala-D-Ala Carboxypeptidase

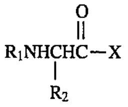

(Im)

wherein X is $X_1$ or $X_2$, $R_4$ is the side chain of D-ala, $R_5$ is deleted and Y is OH or $OR_3$, $R_2$ is the side chain of D-ala, $R_1$ is $P_2$-$P_g$ with $P_2$ being (Nα,ε)-di-Ac-Lys or Groups E and C with (Nα,ε)-di-Ac-Lys being preferred, $P_g$ is an optional Group K amino protecting group with Ac being preferred. The preferred compounds are:

(Nα,ε)-di-Ac-Lys-D-Ala[$CF_2$-(D)-Ala]OH,
(Nα,ε)-di-Ac-Lys-D-Ala[$CF_2$-D-Ala]OMe
(Nα,ε)-di-Ac-Lys-D-Ala-$CHF_2$,
(Nα,ε)-di-Ac-Lys,D-Ala-$CF_2COOEt$, and
(Nα,ε)-di-Ac-Lys-D-Ala$CF_3$.

The compounds embraced by formula (Im) are antibacterial agents particularly useful against gram negative organisms. For their end-use application, the potency and other biochemical parameters of the enzyme inhibiting characteristics of the compounds of (Im) is readily ascertained by standard biochemical techniques well known in the art. Actual dose ranges for their specific end-use application will, of course, depend upon the nature and severity of the disease state of the patient or animal to be treated as determined by the attending diagnostician. It is to be expected that the general end-use application dose range will be about 0.01 to 10 mg per kg per day for an effective therapeutic effect.

The compounds of Formula I which are useful as inhibitors of Cathepsin B are represented by the structural formula

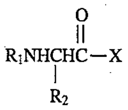

(In)

wherein X is $X_1$ or $X_2$ with $X_1$ being preferred and $CF_3$ and COOH being particularly preferred and when X is $X_2$, $R_4$ is a side chain selected from the amino acids of Group E with the side chain of Leu being preferred, $R_5$ is selected from Groups G, E or F with Gly being preferred and Y is OH, $R_1$ generically is (a)-$P_2$-$P_g$ or (b)-$P_2$-$P_3$-$P_g$ wherein for (a) $P_2$ is selected from Groups E and F with Phe being preferred and $P_g$ is selected from Group K with CBZ being preferred, and (b) $P_2$ is selected from Groups E and F with Leu being preferred, -$P_3$ being selected from groups E and F with Leu being preferred and $P_g$ is selected from Group K with Ac being preferred, $R_2$ is a side chain of an amino acid selected from Group A and J or $ThrCOCH_2\phi$, with the side chain of Arg being preferred. The preferred compounds are:

Ac—Leu—Leu—Arg[$CF_2$—Leu] Gly—OH,

CBZ—Phe—Arg[$CF_2$—Leu] Gly—OH,

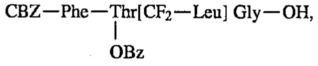

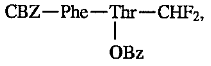

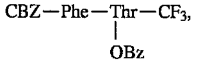

and

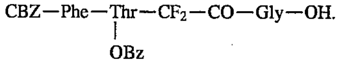

The compounds of formula (In) inhibit Cathepsin B and therefore are useful in treating excessive cell growth disease states such as, for example, being useful in treating benign prostate hypertrophy, prostatic carcinoma, in treating psoriasis and in their use as abortifacients. For their end-use application, the potency and other chemical parameters of the enzyme inhibiting characteristics of the compounds of (In) is readily ascertained by standard biochemical techniques well known in the art. Actual dose ranges for their specific end-use application will, of course, depend upon the nature and severity of the disease state of the patient or animal to be treated as determined by the attending diagnostician. It is to be expected that the general end-use application dose range will be about 0.01 to 10 mg per kg per day for an effective therapeutic effect.

The compounds of Formula I which are useful as inhibitors of renin are representative by the structural formula

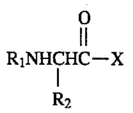
(Io)

with the proviso that the depicted carbonyl moiety attached to X may exist in its chemically reduced form, i.e.,

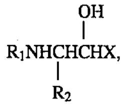

wherein X is $X_1$ or $X_2$, which when X is $X_1$, $CF_3$, COOH or COOMe are preferred and when X is $X_2$, $R_4$ is a side chain of an amino acid selected from Groups E, F or G with the side chain of Val being preferred, $R_5$ is $P'_2$-$P'_3$-$P'_4$, $P'_2$ being from Groups E, F or is deleted, with $P'_3$ being selected from Groups E or F or is deleted with Ile being preferred and $P'_4$ being selected from Groups E, C or F or is deleted with His being preferred and Y is OH or $NH_2$, $R_2$ is a side chain of an amino acid selected from Groups E or F or is cyclohexylmethylene with Leu being preferred, $R_1$ is $-P_2$-$P_3$-$P_4$-$P_5$-$P_g$ wherein $P_2$ is selected from Groups E, C or F with His being preferred, $P_3$ is selected from Groups E or F with Phe being preferred, $P_4$ is selected from Groups E, D, F or is deleted with Pro being preferred, $P_5$ is selected from Groups E, C, F or is deleted with His being preferred, and $P_g$ is selected from Group K with MeOSuc being preferred. The preferred compounds are:

CBZ-Nal(1)-His-Leu-$CHF_2$,
CBZ-Nal(1)-His-Leu-$CF_3$,
CBZ-Nal(1)-His-Leu-$CF_2$-COOEt,
MeOSuc-His-Pro-Phe-His-Leu-[$CF_2$-Val]Ile-His-OH,
MeOSuc-Pro-Phe-His-Leu-[$CF_2$-Val]Ile-His-OH,
MeOSuc-His-Phe-His-Leu-[$CF_2$-Val]Ile-His-OH,
MeOSuc-His-Pro-Phe-His-Leu-[$CF_2$-Val]Ile-OH,
MeOSuc-His-Pro-Phe-His-Leu-[$CF_2$-Val]His-OH,
BOC-His-Pro-Phe-His-Leu[$CF_2$-Val]-Ile-His-OH,
BOC-His-Pro-Phe-His-Leu-[$CF_2$-CO]-Ile-His-$NH_2$, and
BOC-Pro-Phe-His-Leu[$CF_2$-Val]-Ile-His-$NH_2$.

The compounds of Formula (Io) inhibit renin and therefore are used as antihypertensive agents useful in treating hypertension. For their end-use application, the potency and other biochemical parameters of the enzyme inhibiting characteristics of the compounds of (Io) are readily ascertained by standard biochemical techniques well known in the art. Actual dose ranges for their specific end-use application will, of course, depend upon the nature and severity of the disease state of the patient or animal to be treated as determined by the attending diagnostician. It is to be expected that the general end-use application dose range will be about 0.01 to 10 mg per kg per day for an effective therapeutic effect.

The compounds of Formula I which are useful as inhibitors of pepsin are represented by the structural formula

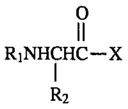
(Ip)

with the proviso that the depicted carbonyl moiety attached to X may exist in its chemically reduced form, i.e.,

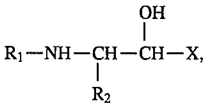

wherein X is $X_1$ and $X_2$, which when X is $X_1$ $-CF_2H$, $CF_3$ and $CONH_2$ are preferred, and when X is $X_2$ then, $R_4$ is a side chain of an amino acid selected from the Groups E, G and F with the side chain of Gly being preferred, $R_5$ is selected from Groups E and F with Ala being preferred and Y is $-NHCH_2CH(CH_3)_2$ or $-NHCH_2CH_2CH(CH_3)_2$, R is $-P_2$-$P_3$-$P_g$ with $P_2$ being selected from Groups E or F with Val being preferred, $P_3$ is selected from Groups E or F with Val being preferred or is deleted and $P_g$ is selected from Group K preferably Iva, and $R_2$ is a side chain of an amino acid selected from Groups E and F with the side chain of Leu being preferred.

The preferred compounds are:

Iva—Val—Leu—$CF_2$—CO—Ala—NH—$CH_2CH_2CH(CH_3)_2$, 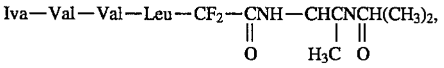

Iva—Val—Val—Leu[$CF_2$—Gly]—N(Me)Ala—$NHCH_2CH_2CH(CH_3)_2$,

Iva—Val—Val—Leu—$CHF_2$, and Iva—Val—Val—Leu—$CF_3$.

The compounds of the formula (Ip) inhibit pepsin and therefore exert an antiulcer effect useful in the treatment and prevention of ulcers. For their end-use applica-tion, the potency and other biochemical parameters of the enzyme inhibiting characteristics of the compounds of (Ip) are readily ascertained by standard biochemical techniques well known in the art. Actual dose ranges for their specific end-use application will, of course, depend upon the nature and severity of the disease state of the patient or animal to be treated as determined by the attending diagnostician. It is to be expected that the general end-use application dose range will be about 0.01 to 10 mg per kg per day for an effective therapeutic effect.

The compounds of formula I which are useful as inhibitors of Cathepsin D are represented by the structural formula

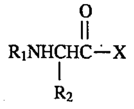
(Iq)

wherein X is $X_1$ or $X_2$ which when X is $X_1$, the preferred groups are $-CO_2R_3$ or $-CF_3$, and when X is $X_2$, $R_4$ is a side chain of an amino acid selected from Groups E and F with the side chain of Phe being preferred, $R_5$ is selected from Groups E and F with Ala being preferred, Y is $-NH(CH_2)_2CH(CH_3)_2$ or $-NHCH_2CH(CH_3)_2$, R is $-P_2-P_3-P_g$ with $P_2$ being selected from Groups E and F, with Val being preferred, $P_3$ is selected from Groups E and F with Val being preferred, and $P_g$ is selected from Group K with CBZ eing preferred, and $R_2$ is a side chain of an amino acid selected from Groups E and F, with the side chain of Phe being preferred. The preferred compounds are:

CBZ-Val-Val-Phe-$CF_2$-CO-Ala-Iaa,
CBZ-Val-Val-Phe-$CF_2$H,
CBZ-Val-Val-Phe-$CF_3$,
CBZ-Val-Val-Phe[$CF_2$-Phe]Ala-$NH(CH_2)_2CH(CH_3)_2$,
CBZ-Val-Val-Phe[$CF_2$-Phe]Ala-$NHCH_2CH(CH_3)_2$, and
with Iaa being isoamyl amide.

As inhibitors of Cathepsin D the compounds of formula (Iq) are useful for the same end-use applications set forth for human leukocyte elastase inhibitors (Ia) and are also useful as antidemyelinating agents useful to prevent and arrest nerve tissue damage. For their end-use application, the potency and other biochemical parameters of the enzyme inhibiting characteristics of the compounds of (In) are readily ascertained by standard biochemical techniques well known in the art. Actual dose ranges for their specific end-use application will, of course, depend upon the nature and severity of the disease state of the patient or animal to be treated as determined by the attending diagnostician. It is to be expected that the general end-use application dose range will be about 0.01 to 10 mg per kg per day for an effective therapeutic effect.

The compounds of formula I which are useful as inhibitors of angiotensin converting enzyme (ACE) are represented by the structural formula

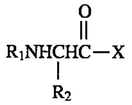

(Ir)

wherein X is only $X_2$ wherein, $R_4$ is a side chain of an amino acid selected from Groups E or G with the side chain of Gly being preferred, $R_5$ is selected from Groups A, B, C, D, E, F and G with Group D being preferred and Y is OH, $R_1$ is selected from Group K with Bz being preferred, $R_2$ is a side chain of an amino acid selected from Group E, F and G with the side chain of Phe being preferred. The preferred species are illustrated as

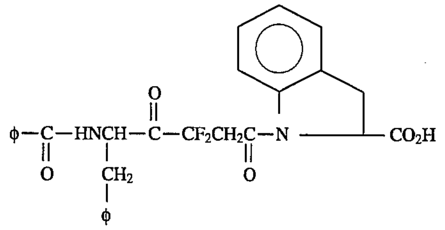

with ϕ being phenyl. This preferred compound is also shown as Bz-Phe[$CF_2$-Gly]Ind-OH.

Other preferred compounds are:
Bz-Phe[$CF_2$-Gly]Pro-OH and
Bz-Phe-$CF_2$-CO-Pro-OH.

The compounds of formula (Ir) inhibit ACE and are therefore useful as antihypertensives useful in treating hypertension. For their end-use application, the potency and other biochemical parameters of the enzyme inhibiting characteristics of the compounds of (Ir) are readily ascertained by standard biochemical techniques well known in the art. Actual dose ranges for their specific end-use application will, of course, depend upon the nature and severity of the disease state of the patient or animal to be treated as determined by the attending diagnostician. It is to be expected that the general end-use application dose range will be about 0.01 to 10 mg per kg per day for an effective therapeutic effect.

The compounds of Formula I which are useful as inhibitors of enkephalinase are represented by the structural formula

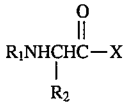

(Is)

wherein X represents $X_2$ wherein, $R_4$ is a side chain of an amino acid selected from Group E or F with the side chain of Phe being preferred, $R_5$ is selected from the Groups E or F or zero with the proviso that when $R_5$ is zero, Y is $NH_2$, with Met being preferred and Y is $NH_2$ or OH, preferably OH when $R_5$ is Met or other α-amino acid, $R_1$ generically is $-P_2-P_3$, with $P_2$ being Gly and $P_3$ being selected from Group F or is deleted with Tyr being preferred, and $R_2$ is the side chain of Gly.

The preferred compounds are:
H-Tyr-Gly-Gly-$CF_2$-CO-Phe-Leu-OH,
H-Tyr-Gly-Gly[$CF_2$-Phe]Met-OH,
H-Tyr-Gly-Gly[$CF_2$-Phe]Leu$NH_2$, and
H-Tyr-Gly-Gly-$CF_2$-CO-Leu-OH.

The compounds of formula (Is) inhibit enkephalinase and therefore are useful as analgesics. For their end-use application, the potency and other biochemical parameters of the enzyme inhibiting characteristics of the compounds of (Is) are readily ascertained by standard biochemical techniques well known in the art. Actual dose ranges for their specific end-use application will, of course, depend upon the nature and severity of the disease state of the patient or animal to be treated as determined by the attending diagnostician. It is to be expected that the general end-use application dose range will be about 0.01 to 10 mg per kg per day for an effective therapeutic effect.

The compounds of Formula I which are useful as inhibitors of pseudomonas elastase are represented by the structural formula

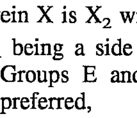

(It)

wherein X is $X_2$ with, $R_4$ being a side chain of an amino acid selected from Groups E and F with the side chain of Ile being preferred, $R_5$ is selected from Groups E and G with Ala being preferred and Y is $NH_2$, $R_1$ is $-P_2-P_g$ with $P_2$ being selected from Group E with Ala being preferred, $P_g$ is selected from Group K with MeOSuc being preferred, $R_2$ is a side chain of an amino acid selected from Groups E and G with the side chain of Ala being preferred. The preferred compounds are:

MeOSuc-Ala-Ala[$CF_2$-Ile]Ala-$NH_2$ and

MeOSuc-Ala-Ala-$CF_2$-CO-Ile-Ala-$NH_2$.

The compounds of the Formula (It) inhibit Pseudomonas elastase and therefore are useful as antibacterial agents particularly useful against infections caused by pseudomonas bacteria. For their end-use application, the potency and other biochemical parameters of the enzyme inhibiting characteristics of the compounds of (It) are readily ascertained by standard biochemical techniques well known in the art. Actual dose ranges for their specific end-use application will, of course, depend upon the nature and severity of the disease state of the patient or animal to be treated as determined by the attending diagnostician. It is to be expected that the general end-use application dose range will be about 0.01 to 10 mg per kg per day for an effective therapeutic effect.

The compounds of formula I which are useful as inhibitors of leucine aminopeptidase are represented by the formula

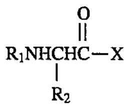

(Iu)

wherein X embraces all of $X_1$ and $X_2$ which when X is $X_1$, $CO_2R_3$ or $-CF_3$ are preferred and when X is $X_2$, $R_4$ is the side chain of an amino acid selected from any Group except K with the side chain of Ala and Group E being preferred, $R_5$ is any Group except K with Ala and Group E being preferred, Y is $NH_2$, $R_1$ is hydrogen, and $R_2$ is a side chain of an amino acid selected from Groups A, B, E, F and J with the side chains of Phe, Leu, Glu, and Arg being preferred. The preferred compounds are:

H-Leu-$CHF_2$,

H-Leu-$CF_2$-COOEt,

H-Arg-$CF_3$,

H-(p-gua)Phe-$CF_3$,

H-Leu-$CF_3$ and H-Leu-COOH,

H-Leu[$CF_2$-Ala]Ala-$NH_2$ and H-Leu-COOMe or Leu-COOH, and

H-Arg-CO-$CF_2$-Phe-OH.

The compounds of formula (Iu) are inhibitors of leucine amino peptidase and therefore are useful as immunostimulants useful in conjunctive therapy in the treatment with other known anticancer agents. For their end-use application, the potency and other biochemical parameters of the enzyme inhibiting characteristics of the compounds of (Iu) are readily ascertained by standard biochemical techniques well known in the art. Actual dose ranges for their specific end-use application will, of course, depend upon the nature and severity of the disease state of the patient or animal to be treated as determined by the attending diagnostician. It is to be expected that the general end-use application dose range will be about 0.01 to 10 mg per kg per day for an effective therapeutic effect.

The compounds of Formula I which are useful asinhibitors of kallikreins, tissue or plasma, are represented by the formula

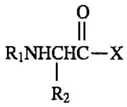

(Iv)

wherein X is $X_1$, $R_2$ preferably is the side chain of Arg, $R_1$ is a peptide $-P_2-P_3$ with $P_2$ being selected from the Groups F and E with Phe being preferred, $P_3$ being selected from Groups C, E or F, the residues of which may be in either the D- or L-configuration.

The preferred compounds of this formula (Iv) are:

D-Pro-Phe-Arg-$CF_2H$,

D-Pro-Phe-Arg-$CF_3$,

D-Pro-Phe-Arg-$CO_2H$, and

D-Pro-Phe-Arg-$CONH_2$.

The compounds of formula (Iv) are inhibitors of the kallikreins, tissue or plasma, and therefore inhibit kinin formations. Kinins, generally known to induce pain and vascular permeability associated with inflammation and infection, e.g., bacterial and viral, the inhibition of the kinin formation renders these compounds useful in the alleviation of pain and inflammation. Furthermore, these compounds are useful as male contraceptives in that they will dramatically interfere with normal sperm function. In their end-use application dose range will be about 0.01 to 10 mg per keg per day for an effective therapeutic effect.

Having defined the scope of compounds embraced within the generic formula I and within the individual subgeneric groups of each of the 21 enzymes, the manner in which such compounds may be prepared will hereinbelow be described as illustrated. The preparation of the compounds of formula I may be achieved using standard chemical reactions analogously known to be useful for the preparation of a variety of known peptides. Indeed, for the most part, once certain key intermediate α-amino acid derivatives are prepared, the procedures for obtaining the final products may readily be effected using standard techniques known to those skilled in the field of peptide chemistry. For this purpose, a handy reference text for these techniques is the 1985 "The Practice of Peptide Synthesis" by M. Bodanszky and A. Bodanszky, wherein the parameters and techniques affecting the selection, use and removal of protective groups for individual and groups of amino acids is detailed, and which also contains activation andcoupling techniques and other special procedures. However, before the application of these peptide chemistry techniques may be applied, certain key intermediates containing the activated electrophilic ketone moiety must first be prepared. The preparation of the key intermediates is described as follows.

For those compounds wherein $X_1$ represents either $-CF_2H$ or $-CF_3$, the key intermediates required for the application of the standard peptide coupling techniques are compounds of formula IIIa-b

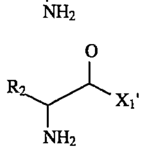

IIIa

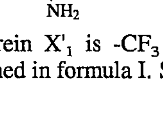

IIIb wherein $X'_1$ is $-CF_3$ or $-CF_2H$, and $R_2$ is as previously defined in formula I. Similarly, designations $R_1$, $R_2$, $R_3$, $R_4$, $R_5$ and Y shown in the following reaction schemes A through D are as defined in formula I, except that any subgeneric or other modifications thereof (as in $X'_1$) are highlighted by the use of a primed symbol with a specific designation for such modified symbol. The preparation and application of these compounds is depicted by Reaction Scheme A.

REACTION SCHEME A

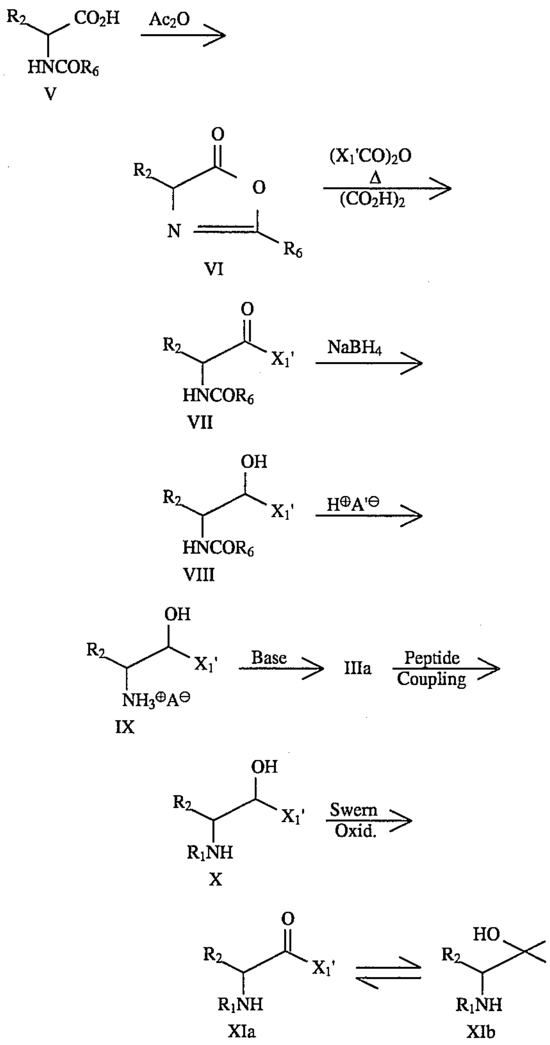

wherein $R_6$ is alkyl, phenyl or other equivalent moiety, and $X'_1$ is $-CF_2H$ or $-CF_3$.

In general, the formation of the substituted azlactones (VI) is effected from the N-protected amino acids (V) by standard reaction conditions wherein the amino acid derivative (V) is heated in the presence of an acid an-hydride. The so-produced azlactone (VI) is reacted with a di- or trifluoroacetic acid anhydride or acid halide to give a fluorinated intermediate which (with or without isolation) is treated with anhydrous oxalic acid toproduce the N-protected fluorinated ketone (VII) whereupon the ketone is chemically reduced to its alcoholic amide (VIII) is cleaved under standard acidic conditions to yield its amide acid salt (e.g., its hydrochloride (IX)). After neutralization, the alcohols (IIIa) may be coupled to $R_1$ using standard peptide chemistry techniques to produce compounds (X) which are subjected to the Swern oxidation procedure to obtain the desired products XIa and XIb (the ketone or hydrate respectively). Alternatively, the alcohols (IIIa) may be oxidized to the ketones (IIIb) which are coupled to $R_1$ according to standard peptide chemistry techniques. When employing this alternative route, the amino moiety is first protected with a Boc protecting group, the OH function oxidized to its ketone via Swern oxidation procedures, and then the Boc protecting group removed and the resulting compounds (IIIb) are then coupled to $R_1$.

In effecting the foregoing reactions, standard and well-known techniques analogously known are utilized, for example, the azlactones (VI) are chemically transformed to their di- or trifluoromethyl derivatives (their $X'_1$ derivatives) (VII) by heating the azlactone and the fluoroacetic acid anhydride or acid halide reactants at temperatures of about 30° to 200° C. for about 1–24 hours (although under very mild conditions it may take up to one week) preferably using molar equivalent quantities of the reactants. In the event excess quantities of the anhydride reactant is used, such excess should be removed before the next step and the crude product is treated with anhydrous oxalic acid. The fluorinated ketone is reduced to its alcohol using excess quantities of sodium borohydride or any other suitable reducing agent, e.g., sodium cyanoborohydride. Following reduction, the reaction is quenched and the amide is cleaved understandard acidic conditions in water, alcohol or other hydroxylic solvent. The solution is made basic andextracted to obtain the corresponding alcohol (IIIa).

It is, of course, obvious to one of ordinary skill in the art that the conditions of the steps of Reaction Scheme A may have an impact on the $R_2$ side chain and thus procedures will have to be taken to protect those $R_2$ moieties which are not compatible with the various reaction conditions. For example, $R_2$ moieties which belong to Group E are generally compatible. Similarly, $R_2$ side chain radicals from Groups F, J, and G are compatible. Radicals of Group A need protection. Since arginine may be considered as a derivative of ornithine, the ornithine derivative may first be prepared and then converted to the arginine side chain otherwise the guanidino function of the arginine moiety will have to be protected. The Group C radicals of serine, threonine and cysteine must be protected, preferably with an ether (e.g., benzyl ether). Preferably, the -OH and -SH functions of these groups are protected before the azlactone is formed. The (X) intermediate wherein $X'_1$ is $-CF_3$ and $R_2$ is H is known (*Journal of the American Chemical Society*, 70, 143 (1948)), and thus the $CF_2H$ analogs may be prepared using the analogous procedures. The carboxyl moiety of the Group B $R_2$ side chains must also be protected. The need for the selection of the protecting groups and the reaction conditions for compatability, selective cleavage and other factors obvious to those skilled in the art are well known and appreciated by those skilled in this field of chemistry.

For those compounds wherein $X_1$ represents $CO_2R_3$, $CONR_3$ or $COR_5Y$, the key intermediates required for the application of the standard peptide coupling techniques have the formula

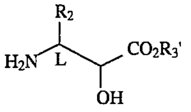

with $R'_3$ being as previously defined for $R_3$ except that H is omitted from its definition.

The preparation and application of these compounds may be depicted by the following reaction scheme. (NB. The desired stereochemistry at the N-substituted carbon is obtained unless otherwise noted.)

REACTION SCHEME B

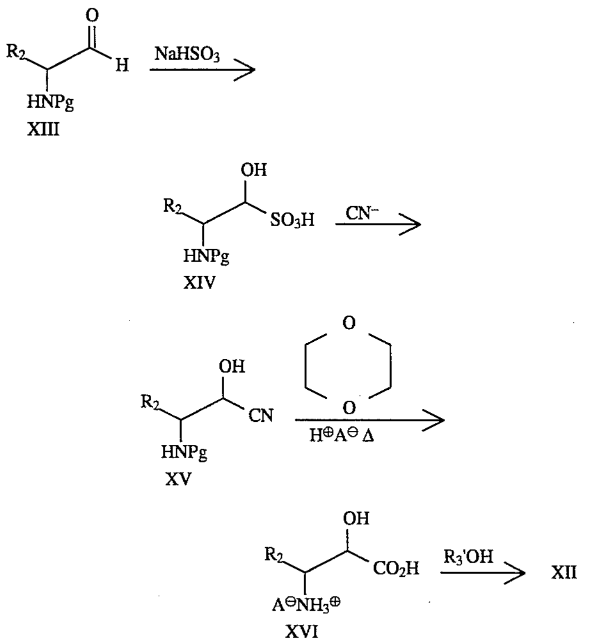

B(a):

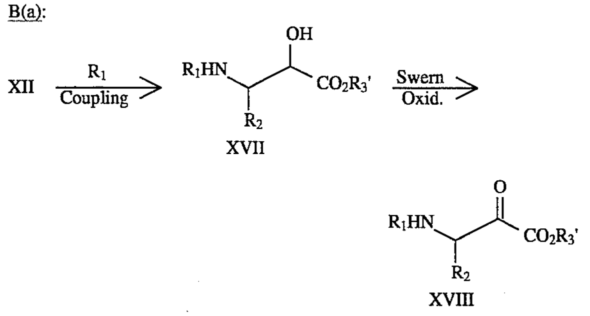

B(b):

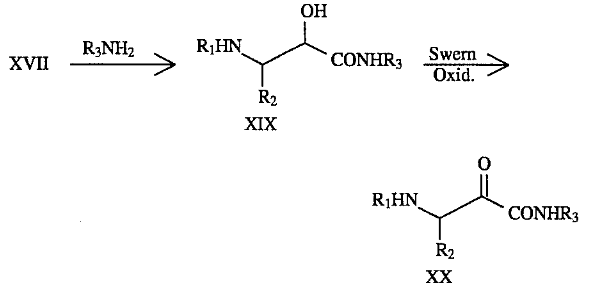

B(c):

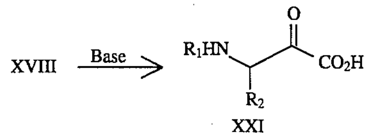

B(d):

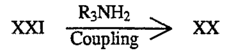

-continued

REACTION SCHEME B

B(e):

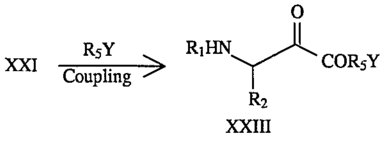

B(f):

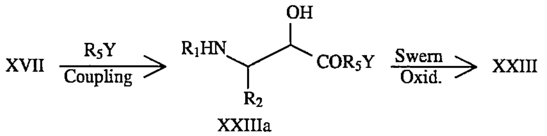

wherein $A^{\ominus}$ is the anion of the acid employed and $R'_3$, except for the exclusion of H, is as defined for $R_3$, and $P_g$ is a suitable amino moiety protecting group, and in XXV of reaction (b) $R^1$ is the same as

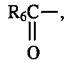

and $R'_5$ is other than zero.

Compounds XIII are generally known starting materials. (In general, such materials may be prepared by converting the appropriate L-amino acid to its ester, preferably its methyl ester by standard esterification procedures (e.g., $SOCl_2$ in the presence of alcohol), the ester is N-protected, preferably with di-t-butyl dicarbon-ate (Boc). The so-protected $R_2$-amino acid is chemically reduced to the desired aldehydic form (XIII) of the N-protected amino acid, preferably with diisobutylaluminum hydride (Dibal); all such procedures being by techniques well known in the art. Of course, other procedures for obtaining the same end products are readily available by techniques well known in the art.

The reaction steps of Reaction Scheme B also use standard and well known techniques. For example, conversion of the aldehydes (XIII) to the corresponding cyanohydrin is effected by reaction with a bisulfite (e.g., $NaHSO_3$) to obtain a bisulfite addition product XIV which is treated with a metallocyanide (e.g., KCN) to produce the corresponding cyanohydrin (XV). Of course, other procedures are readily available for the conversion of the aldehyde to the cyanohydrin derivatives (XV). The cyanohydrins are heated in a mixture of an aqueous acid and water miscible solvent such as an ether (preferably dioxane) to form the desired hydroxy acid (XVI) as a mixture of its diastereoisomers. These compounds are subjected to neutralization and purification by standard procedures, such as ion exchange resin chromatographic techniques, to yield products which are esterified to obtain the desired key intermediates (XII).

In effecting B(a), the amino esters (XII) are coupled with the $R_1$ moiety according to standard peptide coupling techniques, taking care that the protective group utilized (if any) are selectively cleavable over the $CO_2R'_3$ moiety. Oxidation of the coupled products is best achieved with the Swern reaction to convert the alcohol to its keto form which, as noted above, can exist in equilibrium with its hydrate.

In effecting B(b), the ester (XVII) is treated with an amine ($R_3NH_2$) to give the amide (XIX) which may be oxidized via the Swern oxidation procedures to its keto amide (XX). In this instance oxidation conditions other than that of the Swern conditions may also be employed (e.g., oxidation with pyridinium dichromate).

In effecting B(c), the keto ester (XVIII) is treated with a base (e.g., LiOH) to give its keto acid (XXI) except in the case when $R_1$ contains a terminal methoxysuccinyl moiety in which case the $R'_3$ must be selectively clearable, e.g., $R'_3$ ought to be t-butyl or benzyl which are selectively cleaved under acidic or hydrogenolysis conditions respectively. In effecting step B(d) the keto acid (XXI) is converted to its amide by standard coupling procedures.

In effecting B(e), the acid is coupled with $R_5Y$ according to standard procedures, taking care to protect and deprotect as needed in the light of the various groups in the definition of $R_5$ and Y. In reaction B(f) the ester (XVII) is converted to an amide and the amide oxidyzed according to Swern oxidation conditions.

As noted above (following the discussion of Reaction Scheme A), the conditions of the foregoing reactions in the obtention of the desired intermediates and final products of Reaction Scheme B are effected taking care that the $R_2$-side chain radicals are compatible. Although Groups E, F and G are generally compatible, protection of some $R_2$ side chains will be necessary. For example, histidine will have to be protected, while tyrosine and tryptophan ought be protected in order to improve overall yields. Again, ornithine must have its terminal delta amino group protected and ornithine may be converted to arginine. A protecting group would also be needed on a guanidino group. All amino aids, e.g., cysteine and threonine having reactive groups in their side chain preferably are protected.

In the preparation of those compounds wherein $X_2$ is

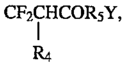

the intermediates will be thos compounds of the formulae

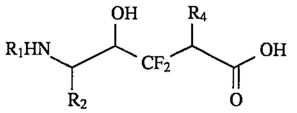
XXIVa

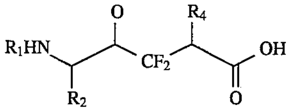
XXIVb which compounds may be prepared and applied according to Reaction Scheme C.

REACTION SCHEME C

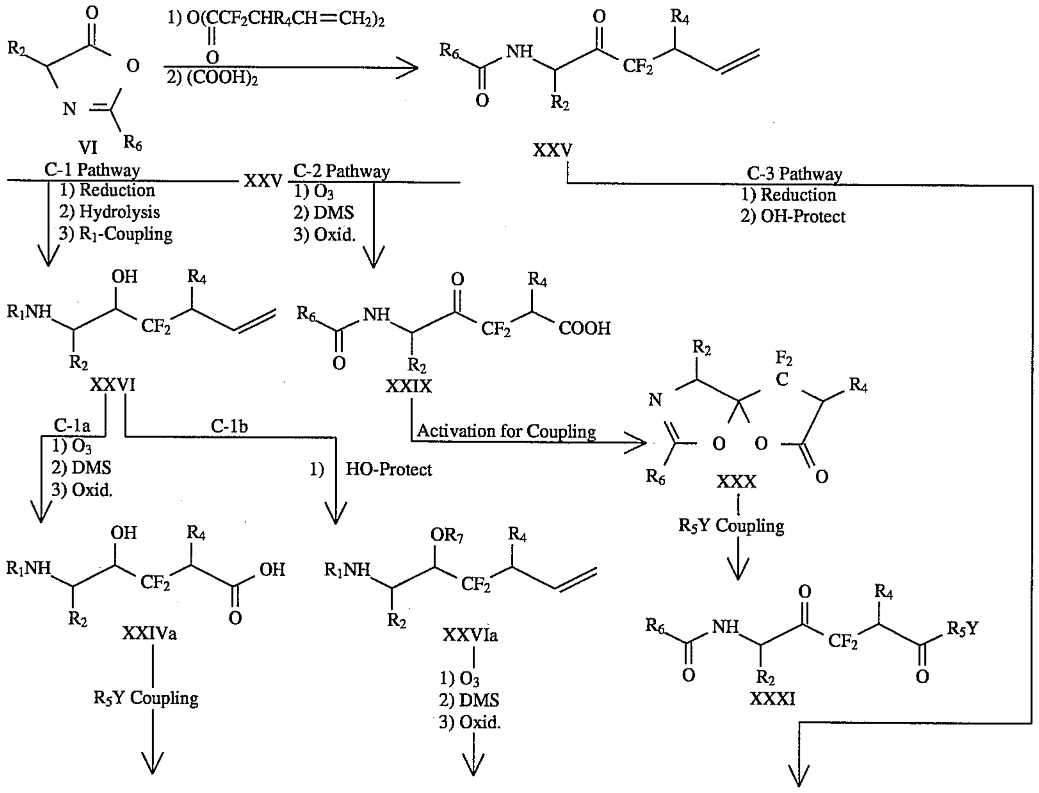

-continued
REACTION SCHEME C

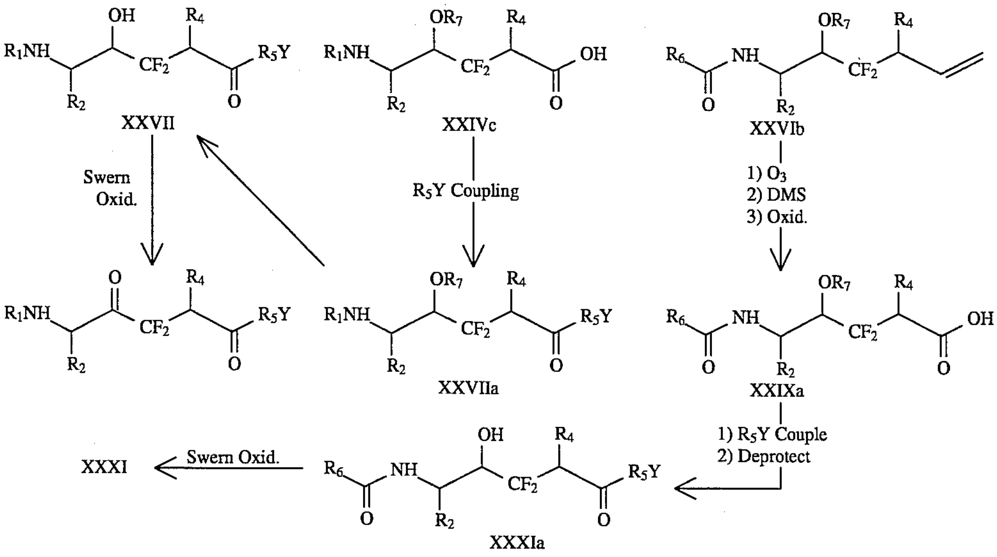

The azlactone (VI) is prepared as in Reaction Scheme A and the steps going from VI to XXV are analogous to those of that Scheme except that the azlactone is treated with an unsaturated fluorinated carboxylic acid anhydride, and the product is treated with anhydrous oxalic acid to produce compounds XXV. Utilizing these intermediates (XXV) several pathways may be utilized to obtain the desired products. In one pathway (C-1) the intermediate is sequentially subjected to a) a chemical reduction of the electrophilic ketone, and b) hydrolysis of the amide by standard procedures prior to coupling the $R_1$ moiety. The coupling is readily accomplished using standardpeptide chemistry coupling procedures (already referenced) to produce compounds of formula XXVI these intermediates are also available for alternate pathways, i.e., C-1a or C-1b. In pathway C-1a the intermediates are sequentially treated with (a) ozone according to standard ozonolysis procedures to produce the corresponding ozonide, (b) treatment with dimethylsulfide to convert the ozonide to its aldehydic form and (c) oxidation, preferably using the Jones oxidation procedure to produce compounds of formula XXIVa. These compounds (XXIVa) are sequentially subjected to (a) $R_5Y$ coupling and (b) Swern oxidation reactions according to already described standard procedures. In those instances wherein it is desired to first protect the hydroxy group, pathway C-1b is available. This pathway essentially mimics C-1a except that the hydroxy function is protected prior to ozonolysis and the hydroxy protecting group (i.e., $R_7$) is removed in preparation for the Swern oxidation reaction. Typical protecting groups compatible with the described reactions can be used. Preferably the methoxyethoxymethyl group is utilized and is readily removed prior to the Swern oxidation by standard techniques such as by treatment with Zn $Br_2$.

In pathway C-2 the intermediates are directed subjected to the above described sequential reactions (ozonolysis, treatment with DMS, and oxidation) to produce compounds of formula XXIX which in preparation for $R_5Y$ coupling are converted to the spiro lactones of formula XXX. Coupling, and deprotection (if necessary) produce the desired compounds XXXI using standard techniques.

Pathway C-3, a variation of pathway C-1b, first reduces the electrophilic ketone to a hydroxy function which is protected with a suitable protecting group (e.g., methoxyethoxymethyl) and the resulting compounds XXVI and subjected to (a) ozonolysis, treatment with DMS, and the Jones oxidations, (b) R5Y coupling and deprotectionreactions, and (c) Swern oxidation, (all of these reactions being done according to the above described procedures for these reactions) to produce the desired compounds of formula XXXI.

In those instances wherein difluorinated acid anhydrides are required for the preparation of the fluoro-methyl azlactones, such anhydrides may be prepared by reacting tetrafluoroethylene ($F_2C{:}CF_2$) with an $R_4CH{=}CHCH_2OH$ reactant in the presence of a base (e.g., NaH) and the so-desired $R_4CH{=}CHCH_2OCF_2$-$CF_2H$ intermediate is treated with butyllithium to produce an acid fluoride

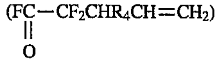

which is converted to its anhydride by standard procedures. Here again, it is obvious that compatibility features must be facilitated to ensure that the relevant groups can withstand the butyllithium reaction; thus the $R_4$ moiety has to be protected when incompatible with the butyllithium reaction.

For those compounds wherein $X_2$ represents

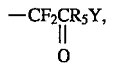

the key intermediates useful for the preparation of the compounds of formula I bearing this group will be of the formulae

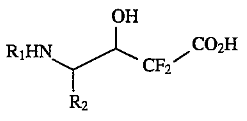

XXXII

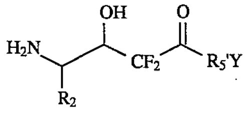

XXXIII the preparation and application of which is depicted by reaction Scheme D.

REACTION SCHEME D

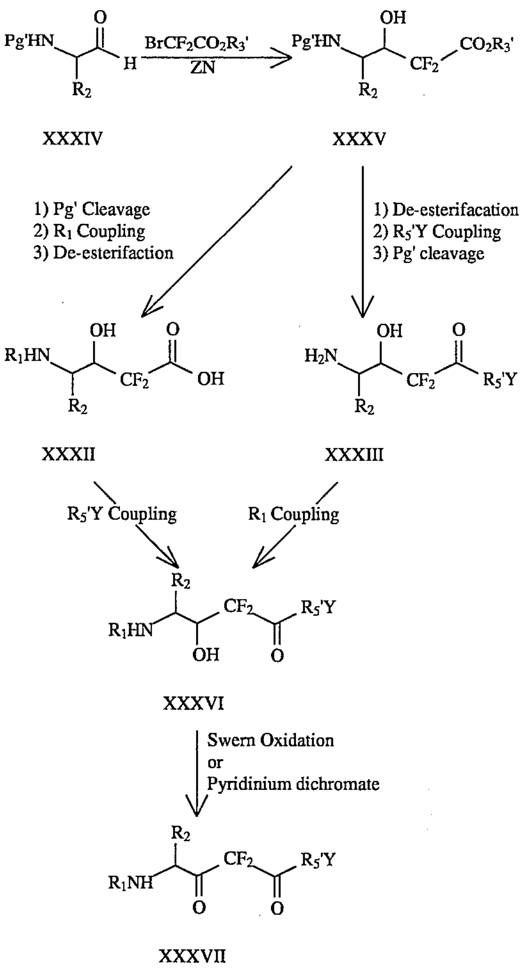

wherein $P'_g$ is a protecting group suitably stable to the reaction steps involved and which is selectively cleaved following $R_5Y$ coupling and the initial alkylation of XXXIV. $R'_5Y$ is as defined for $R_5Y$ except that it optionally contains a protecting group.

Following the initial step of alkylating the N-protected aldehyde of formula XXXIV with an appropriate halide in the presence of zinc, the steps following the obtention of compounds XXXV follow the analogous proce-dures already described for Reaction Schemes A-C.

Having generally described the procedures by which the compounds of this invention may be prepared, the following specific examples serve to further illustrate the standard techniques and procedures which may be utilized to prepare the enzyme inhibitors of this invention (I).

EXAMPLE 1

N[1]-(2-Hydroxy-3,3-difluoro-1-isobutyl-5-hexenyl)-N[2]-isovaleryl valinamide

To a solution of 0.621 g (3 mmol) of 6-amino-4,4-difluoro-8-methyl-1-nonen-5-ol (obtained from the corresponding HCl salt by treatment of aqueous solution with 4N NaOH and extracted with $Et_2O$) and 0.603g (3 mmol) of N-isovaleryl valine in 30 ml THF at 0° C. was added 0.62 g of dicyclohexyl carbodiimide. The mixture was stirred for 15 hours at 25° C., filtered and the filtrate concentrated to yield a semisolid which was dissolved in $CH_2Cl_2$. The organic layer was washed with 1N HCl aqueous $KHCO_3$ and then brine, dried ($MgSO_4$) and flash evaporated to afford a solid, which was purified further by chromatography in $SiO_2$($CHCl_3$/$Et_2O$ (2:1)). The product containing fractions were combined, flash evaporated to give the desired product. Rf 0.15 ($CHCl_3$/$Et_2O$) (2:1)).

EXAMPLE 2

3-Phenacetylamino-1,1,1-trifluoro-2-propanol

To a mixture of 1.3 g of 3-amino-1,1,1-trifluoro-2-propanol HCl and 1.62 g of triethylamine in 26 ml of THF at 0° C. under nitrogen was added dropwise a solution of 1.27 g of phenacetylchloride in 5 ml THF. The reaction mixture was allowed to warm to 25° C. and then stirred for 1 hour. The mixture was diluted with $CH_2Cl_2$ and washed with $H_2O$, twice with 0.1N HCl, and then brine. After drying ($MgSO_4$), the solvent was flash evaporated and the residue (1.8 g) recrystallized from $CH_2Cl_2$ to yield 1.4 g of product; m.p. 96° C.

EXAMPLE 3

N[1]-(2-Hydroxy-3,3,3-trifluoro-1-isopropylpropyl) N[2]-phenylmethyloxycarbonyl-prolinamide To a mixture of 1.1 g of N-phenylmethyloxycarbonyl proline TDO-ester (Cf Hollitzer, Seewald and Steglichm Ang. Int. Edit. 1976, Vol. 15, 444) and 0.42 g of 3-amino-1,1,1-trifluoro-4-methyl-2-pentanol hydrochloride in 50 ml of $CH_2Cl_2$ was added dropwise 0.40 g of triethylamine. After stirring for 14 hours at 25° C., aqueous $KHSO_4$ was added, the layers separated and the organic layer washed with aqueous $KHSO_4$, aqueous $KHCO_3$, $H_2O$ and then brine (2x). After drying ($MgSO_4$), solvents were flash evaporated to yield 0.54 g of a solid residue which was recrystallized in Et20 to give 0.24 g of the analytically pure expected amide; m.p. 99° C.

EXAMPLE 4

3-tert-Butyloxycarbonylamino-1,1,1-trifluoro-5-methyl-2-hexanol

A mixture of 0.5 g of 3-amino-1,1,1-trifluoro-5-methyl-2-hexanol HCl, 0.5 g of di-tert-butyl dicarbonate and 0.45 g of $KHCO_3$ in 1.6 ml in 1.6 ol of $H_2O$/dioxane (1:1) was stirred at room temperature for 14 hours. Workup in $Et_2O$/$H_2O$ gave, after washing of the organic layer with aqueous $NaHSO_4$, $H_2O$ and brine and drying ($MgSO_4$) followed by flash evaporation of the solvents 0.55 g of the expected Boc derivative, Rf 0.44 ($Et_2O$/pentane (1:1)).

EXAMPLE 5

3-Phenacetylamino-1,1,1-trifluoro-2-propanone

To a solution of 0.84 g of oxalyl chloride in 5 ml of $CH_2Cl_2$ at −55° C. (inside temperature) was added 1.03 g of dimethylsulfoxide in 1 ml of $CH_2Cl_2$. After 5 minutes at −55° C., 1.0 g of 3-phenacetylamino-1,1,1-trifluoro-2-propanol in 5 ml $CH_2Cl_2$ and 0.2 ml of DMSO were added. The mixture was stirred for 15 minutes at −55° C. and then triethylamine was added to adjust the pH to 7.0. The mixture was allowed to warm to 25° C., diluted further with $CH_2Cl_2$ and washed with $H_2O$ and then 1N HCl. The organic layer wasdried ($MgSO_4$), flash evaporated to yield the amide ketone, which was purified further by chromatography on $SiO_2$ ($CHCl_3/Et_2O$ (2:1)). Rf 0.29. The product containing fractions were combined and solvent was evaporated under reduced pressure to yield the desired product as a mixture of ketone and hydrate.

EXAMPLE 6

3-tert-Butyloxycarbonylamino-1,1,1-trifluoro-5-methyl-2-hexanone

The named product was prepared by the procedure of example 5 except that 3-tert-butyloxycarbonylamino-1,1,1-trifluoro-5-methyl-2-hexanol is used in place of 3-phenacetylamino-1,1,1-trifluoro-2-propanol.

EXAMPLE 7

$N^1$-(2-Oxo-3,3-difluoro-1-isobutyl-5-hexenyl)-$N^2$-isovaleryl valinamide

To a solution of 0.1 ml of oxalyl chloride in 2.5 ml of $CH_2Cl_2$ cooled to −55° C. was added 0.17 ml of DMSO in 2.5 ml of $CH_2C_12$. After stirring for 5 minutes at −55° C., 0.295 g of N'-(2-hydroxy-3,3-difluoro-isobutyl-5-hexenyl)-$N^2$-isovaleryl valinamide, in a mixture of 2 ml of $CH_2Cl_2$ and 0.4 ml of DMSO, were added. The mixture was stirred for 15 minutes at −55° C. and then triethylamine (about 0.5 ml) was added to adjust the pH of the solution to 8. The mixture was allowed to warm to room temperature, then diluted with $CH_2Cl_2$ and washed with $H_2O$, then with 1N HCl. The organic layer was dried ($MgSO_4$), then flash evaporated to yield 0,270 g of the expected ketone. Rf 0.3 ($CHCl_3/Et_2O$ (2:1)).

EXAMPLE 8

5-Benzoylamino-3,3-difluoro-4-oxo-6-phenylhexanoic acid

A solution of (2-benzoylamino-4,4-difluoro-7-phenyl-6-hepten-3-one (1.72 g, 5 mmol) in dichloromethane (200 ml) was treated with $O_3$ at −78° C. for 12 minutes (about 6 mmol $O_3$). Dimethylsulfide (2 ml, 0.033 mol) was added and the solution allowed to warm to room temperature. After removal of solvents (20 Torr, 30° C. and 0.05 Torr, 30° C.) a slightly colored oil was obtained, which contained free aldehyde, present in about 70% according to H-NMR (CHO versus 2 $CH_2$).

A solution of the oil in acetone (7.5 ml) was treated with a Jones-solution (7.5 ml, 1M $CrO_3/H_2SO_4$) overnight. The organic layer was separated and the aqueous phase extracted with AcOEt (4×10 ml). The combined organic layers were washed with brine, dried ($MgSO_4$) and flash evaporated to yield 1.7 g of the crude acid.

EXAMPLE 9

N1-(2-Oxo-3,3-Difluoro-1-isobutyl-5-carboxylpentyl)-$N^2$-isovaleryl-valinamide

The above-named product was prepared from N'-(2-oxo-3,3-difluoro-1-isobutyl-5-hexenyl)-$N^2$-isovaleryl valinamide by the procedure of example 8.

EXAMPLE 10

6,6-Difluoro-2-phenyl-4-phenylmethyl-3-aza-1.9-dioxaspiro-(4,4)non-2-en-8-one

A solution of crude 5-benzoylamino-3,3-difluoro-4-oxo-6-phenyl hexanoic acid (1.37 g, 3.8 mmol) in 10 ml THF was kept under $N^2$ and cooled to 0° C. Pyridine (0.32 ml, 327 mg, 4.1 mmol) was added slowly. After stirring for 10 minutes at 0° C., the solution was cooled further to −10° C., and oxalyl chloride (0.35 ml, 508 mg, 4 mmol) was added. Gas evolution occurred and the mixture was allowed to warm to 0° C., when a second addition of pyridine (0.32 ml, 327 mg, 4.1 mmol) was added slowly. The mixture was warmed to 40° C. over 30 minutes, when gas evolution had ceased. AcOEt(60 ml) and water (5 ml) were added, the phases separated, and the organic layer washed with 0.1 HCl, aqueous $NaHCO_3$, and water (each 2×5 ml). After drying ($MgSO_4$) the solvents were removed (20 Torr, 40° C.) to yield 1.1 g of crude lactone derivative as a yellow colored oil, which crystallized upon addition of hexane. Recrystallization (AcOEt/hexane, 1:10) afforded 830 mg of pure lactone derivative as colorless needles; mp. 145° C.

EXAMPLE 11

N-(5-Benzoylamino-3,3-difluoro-1,4-dioxo-6-phenylhexyl)-S-indoline-2-carboxylic acid, phenylmethyl ester A mixture of indoline-2-carboxylic acid phenylmethylester hydrochloride (1.16 g, 0.4 mmol) in $Et_2O$ and $H_2O$ (ea. 5 ml) was treated with $Na_2CO_3$ (solid) and stirred for 10 min. The organic layer was separated and the aq. layer extracted with $Et_2O$ (2×10 ml). The combined organic phases were dried ($MgSO_4$) and flash evaporated (20 Torr, 30° C., and then 0.05 Tort, 30° C.). The only residue (960 mg) was dissolved in chloroform (3 ml).

1 ml (about 320 mg, 1.26 mmol) of indolinecarboxylic acid phenylmethyl ester of the above solution was added to 6,6-difluoro-2-phenyl-4-phenylmethyl-3-aza- 1,9-dixoaspiro-(4,4)non-2-en-8-one (365 mg, 1.06 mmol) dissolved in 1 ml of chloroform. After stirring 40 hr. at 40° C., solvents were evaporated (20 Torr, 30° C.) to give an oily residue, which was purified by chromatography on silica gel (10 g, 230–400 mesh, eluent:pentane/AcOEt (20:3)). The product-containing fractions were combined and solvents removed under reduced pressure to give 500 mg of the expected peptide as an oil.

EXAMPLE 12

N-(5-Benzoylamino-3,3-difluoro-1,4-dioxo-6-phenylhexyl)-(S)-indoline-2-carboxylic acid A mixture of N-(5-benzoylamino-3,3-difluoro-1,4-dioxo-6-phenylhexyl)-S-proline phenylmethyl ester (500 mg, 0.84 mmol) and 100 mg Pd/C in i-PrOH (30 ml) was hydrogenated under atmospheric pressure for 12 hours at 25° C. The mixture was filtered and the filtrate flash evaporated to yield 350 mg (82%) of the expected acid as a colorless oil.

EXAMPLE 13

2,2-Difluoro-4-pentenoic acid anhydride

A suspension of silver oxide in water was prepared by adding a solution of NaOH (1.76 g, 0.044 mol) in water (100 ml) to an aqueous solution of silver nitrate (7.14 g, 0.042 mol in 100 ml), decanting the supernatant liquid, washing the residue with water (3×100 ml) and adding 100 ml of water. To this vigorously stirred suspension was added a solution of 2,2-difluoro-4-pentenoic acid (5.44 g, 0.04 mol) in water (100 ml). After 10 minutes the mixture was filtered and the filtrate concentrated (20 Torr, 30° C.) to afford a solid residue; which was dried over phosphorus pentoxide (0.05 Torr, 50° C., 24 hours) to give 8.4 g (87%) of silver 2,2-difluoro-4-pentenoate; a white amorphous powder. A suspension of 7.3 g (0.03 mol) of the silver salt in 50 ml of dichloromethane was stirred under nitrogen, cooled to 0° C. and then 1.9 g (1.3 ml, 0.015 mol) of oxalyl chloride was added slowly. The cooling bath was removed and the reaction mixture allowed to warm up to roomtemperature. Heating to 40° C. for 30 minutes completed the reaction. Cooled again to room temperature, the supernatant liquid was decanted and the residue washed with dichloromethane (2×5 ml). The organic layers were combined and the solvents removed by distillation at atmospheric pressure. The so-obtained oily residue was then purified by distillation to yield 2.85 g of very hydroscopic 2,2-difluoro-4-pentenoic acid anhydride, bp 78°–80° C./20 Torr.

EXAMPLE 14

2-Benzoylamino-1-phenyl-4,4-difluoro-6-hepten-3-one

A mixture of 2,2-difluoro-4-pentenoic acid anhydride (2.80 g, 0.011 mol) and 2-phenyl-4-phenylmethyl-5(4H)-oxazolinone (2.60 g, 0.0104 mol) was stirred under nitrogen for 20 hours at 60° C. (oil bath temperature) to give a lightly red solution. The reaction mixture was then evaporated (0.05 Torr, 40° C.) to afford a highly viscous oil, to which under exclusion of moisture, anhydrous oxalic acid (1.0 g, 0.011 mol) was added and the mixture was heated for 15 minutes (110°–120° C., oil bath temperature). After the violent gas evolution had ceased, the oil was allowed to cool to 25° C. and then dissolved in a mixture of 40 ml of ethyl acetate and 10 ml of water. The organic layer was separated, washed with aqueous sodium bicarbonate (3x), brine, dried over magnesium sulfate and flash evaporated (20 Tort, 30° C.) to afford a red oily residue (2.4 g), which was purified further by flash chromatography on silica gel (50 g, 230–400 mesh, pentane/ethyl acetate (3:1)), Rf 0.6. The product-containing fractions were combined and evaporated to give 2.2 g of a solid, which was recrystallized (ether acetate/pentane) to yield 2.04 g of 2-benzoylamino-1-phenyl-4,4-difluoro-6-hepten-3-one as white needles (59%); mp. 98° C.

EXAMPLE 15

6-Benzoylamino-4,4-difluoro-8-methyl-1-nonen-5-one

The above-named product was prepared from 2-phenyl-4-isobutyl-5-(4H)oxazolinone by the same procedure of the preceding example (yield 73% as oil).

EXAMPLE 16

N-(3,3,3-trifluoro-2-oxo-1-(phenylmethyl)propyl)benzamide 2.01 g (0.01 mol) of 2-phenyl-4-phenylmethyl-5(4H)oxazolinone and 2.52 g (0.012 mol) of trifluoroacetic anhydride are stirred under $N_2$ for 24 hours at 35°–40° C. (oil bath temperature). After cooling to ambient temperature, the excess of trifluoroacetic anhydride and the acid formed are flash evaporated (0.01 Tort, 30°–50° C.). 1.35 g (0.015 mol) of freshly sublimed anhydrous oxalic acid (0.01 Torr, 80°–100° C.) is added and the mixture heated under stirring to 110°–120° C. (oil bath temperature). After gas evolution hasceased (10–15 minutes) the mixture is allowed to cool to ambient temperature and stirred for about 1–2 minutes with a mixture of ethyl acetate and $H_2O$ (10/1). Phases are separated and the organic layer washed with a solution of $NaHCO_3$ and then brine (each 3×20 ml). Drying ($MgSO_4$) and flash evaporation (20 Tort and 0.01 Torr/30° C.) affords a solid which can be crystallized from ethyl acetate/hexane to yield 2.02 g (63%) of the expected trifluoromethyl ketone:hydrate mixture as a white powder; mp. 163° C.

EXAMPLE 17

N-[3,3-Difluoro-2-oxo-1-(phenylmethyl)propyl]benzamide

The above-named product was prepared in 50% yield by the preceding procedure except that difluoroacetic anhydride was used in place of trifluoroacetic anhydride; m.p. 136° C.

EXAMPLE 18

N-[3,3,3-Trifluoro-2-oxo-(4-nitrophenylmethyl)propyl]benzamide

The above-named product was prepared in 55% yield by the preceding procedure (example 16) except that 2-phenyl-4(4-nitro-phenyl)methyl-5(4H) oxazolinone was used in place of 2-phenyl-4-phenylmethyl-5(4H)oxazolinone:hydrate mixture; m.p. 175° C.

EXAMPLE 19

N-[2-(4-Aminoiminomethyl amino phenyl)-1-trifluoroacetyl ethyl]benzamide, hydrochloride A suspension of 1.77 g (0.0054 mol) of N-benzoyl-(4-guanidino)phenylalanine in 10 ml (1.438 g/0.07 mol) of trifluoroacetic anhydride is stirred at 40K° C. (oil bath temperature) for 20 hours. The clear solution is flash evaporated (0.01 Torr, 40° C.) and treated with anhydrous oxalic acid as described in the synthesis of N-[3,3,3-trifluoro-2-oxo-1-(phenylmethyl)propyl]benzamide, to yield 1.2 g (53%) of the expected trifluoromethyl ketone:hydrate mixture as a white powder; m.p. 96° C.

EXAMPLE 20

N-[3,3,3-Trifluoro-2-oxo-1-(2-methylethyl)propyl]benzamide

The above-named product was prepared in 23% yield by the procedure of example 16 except that 2-phenyl-4-(2-methylethyl)-5-(4H)oxazolinone was used in place of 2-phenyl-4-phenylmethyl-5-(4H)oxazolinone; m.p. 94° C.

EXAMPLE 21

N-{3,3,3-Trifluoro-2-oxo-1[(4-phenylmethyloxycarboxamide)butyl}propyl benzamide

The above-named product (as an oil) was prepared in 56% yield by the procedure of example 16 except that 2-phenyl-4(4-phenylmethyloxycarboxamido)butyl-5-( 4H)oxazolinone was used in place of 2-phenyl-4-phenylmethyl-5-(4H)oxazolinone.

EXAMPLE 22

N,(1-Trifluoroacetyl-3-methyl butyl)benzamide

The above-named product (as an oil) was prepared in 33% yield by the procedure of example 16 except that 2-phenyl-4-isobutyl-5-(4H)-oxazolinone was used in place of 2-phenyl-4-phenylmethyl-5-(4H)-oxazolione.

EXAMPLE 23

N-(3,3,3-Trifluoro-2-oxo-propyl)benzamide

A solution of 7.57 g hippuric acid and 17.4 ml of trifluoroacetic anhydride in 60 ml of anhydrous acetone was stirred at 25° C. for 16 hours under $N_2$ to yield a red precipitate, which is isolated by filtration. Refluxing the red solid in 50 ml of $H_2O$ for 1 hour gave a solution, which was extracted with AcOEt. The organic layer was dried ($MgSO_4$) and flash evaporated to yield crude product which is recrystallized from benzene to give 4.15 g of analytically pure product; m.p. 105° C. (decomp).

EXAMPLE 24

3-Benzoylamino-1,1,1-trifluoro-2-propanol

A solution of 10 g (0.263 mol) of $NaBH_4$ in 100 ml of $H_2O$ was added to 14.8 g (59.4 mmol) of N-(3,3,3-trifluoro-2-oxopropyl)benzamide in 1000 ml of $H_2O$. After stirring for 2 hours at 25° C., the solution was acidified with concentrated HCl (pH 1), basified by adding NaOH pellets (pH 10) and extracted with AcOEt (3×500 ml). After drying ($MgSO_4$), the organic layer was flash evaporated to give 11 g of a white solid, which was recrystallized from $CHCl_3$ to yield 10.0 g (72%) of pure trifluoromethylalcohol; m.p. 156° C.

EXAMPLE 25

6-Benzoylamino-4,4-difluoro-8-methyl-1-nonen-5-ol

The above-named product was prepared from 6-benzoylamino-4,4-difluoro-8-methyl-1-nonen-5-one by example 24 except that the alcohol was purified by chromatography on silica gel (eluent EtOAc/hexane (1/5)); m.p. 110° C.

EXAMPLE 26

3-Benzoylamino-1,1,1-trifluoro-4-methyl-2-pentanol

The above-named product was prepared from N-(3,3,3-trifluoro-2-oxo-1-(1-methylethyl)propyl)benzamide by example 24 in 77% yield; m.p. 150° C.

EXAMPLE 27

3-Benzoylamino-1,1,1-trifluoro-5-methyl-2-hexanol

The above-named product was prepared from N-(1-trifluoroacetyl-3-methylbutyl)benzamide by the procedure ofexample 24 in 80% yield.

EXAMPLE 28

3-Amino-1,1,1-trifluoro-2-propanol hydrochloride

A mixture of 3 g (12.9 mmol) of 3-benzoylamino-1,1,1-trifluoro-2-propanol in 26 ml of $H_2O$, 26 ml of concentrated HCl and 26 ml of ethanol was refluxed for 20 hours, then concentrated under reduced pressure. The residue was dissolved in water and extracted with diethyl ether. The aqueous layer was then concentrated to give a solid residue which was recrystallized from isopropanol/diethyl ether to yield 1.37 g of the fluorinated amino alcohol.

EXAMPLE 29

3-Amino-1,1,1-trifluoro-4-methyl-2-pentanol hydrochloride

The above-named product was prepared from 3-benzoylamino-1,1,1-trifluoro-4-methyl-2-pentanol in 75% yield by the procedure of example 28. Rf 0.37 (AcOEt/$Et_3N$ (20:1)).

EXAMPLE 30

3-Amino-1,1,1-trifluoro-5-methyl-2-hexanol hydrochloride

The above-named product was prepared from the corresponding 3-benzoylamino derivative. m.p. 283° C.; Rf 0.78 (EtOH/$NH_4OH$, (70/30)) by the procedure of example 28.

EXAMPLE 31

6-Amino-4,4-difluoro-8-methyl-1-nonen-5-ol hydrochloride

The above-named product was obtained by the procedure of example 28 in 89% yield from the corresponding 6-benzoylamino derivative.

EXAMPLE 32

4-N-tert-Butoxycarbonylamino 2,2-difluoro 3-hydroxy 6-methyl heptanoic acid ethyl ester To a refluxing suspension of 0.196 g of activated zinc wool in anhydrous tetrahydrofuran (3 ml) is added a solution of 0.618 g (3mmol) of ethyl bromodifluoroacetate in anhydrous THF (1 ml). After the reaction starts, a solution of 0.5 g (2.32 mmol) of N-tert-butoxycarbonyl leucinal is added. The mixture is left at gentle reflux for 1 hour. The reaction mixture is then cooled, quenched by addition of ethyl acetate (10 ml), brine and 1M $KHSO_4$. The organic layer is dried over anhydrous $MgSO_4$, evaporated and purified by flash chromatography (silica gel, 10% EtOAc/cyclohexane) yield, 0.210 g, Rf 0.65 (EtOAc/cyclohexane, 1:1).

EXAMPLE 33

4-N-tert-Butoxycarbonylamino 2,2-difluoro 3-hydroxy 6-methyl heptanoic acid

A solution of 0.0285 g (0.68 mmol) of LiOH, H2O in water (2 ml) is added at 0° C. to a mixture of 0.210 g (0.62 mmol) of 4-N-tert-butoxycarbonylamino 2,2-difluoro 3-hydroxy 6-methyl heptanoic acid, ethyl ester in 1,2-dimethoxyethane (DME) (5 ml). The temperature is allowed to raise slowly to room temperature. The mixture is stirred at room temperature overnight. The mixture is diluted with water (10 ml) washed with diethyl ether (10 ml). The aqueous layer is acidified to about pH 2 with 0.1N HCl, extracted with diethyl ether (2×10 ml). The combined organic layers is washed with brine and dried overanhydrous $MgSO_4$. Filtration and removal of the solvent in vacuo yields the expected acid which is recrystallized from diethyl ether/pentane.

EXAMPLE 34

4-N-tert-Butoxycarbonylamino 2,2-difluoro 3-hydroxy N-(1-isoamylaminocarbonyl ethyl)-6-methylheptanamide To a mixture of 0.194 g (1 mmol) of alanine isoamyl amide hydrochloride in methylene chloride (or DMF) (5 ml) is added 0.101 g (1 mmol) of triethylamine at 0KC. 4-N-tert-butoxycarbonylamino-2,2-difluoro- 3-hydroxy-6-methyl heptanoic acid (0.311 g) and 1-hydroxybenzotriazole (0.202 g) are added, followed by the addition of DCC (0.206 g, 1 mmole) in methylene chloride (5 ml). The reaction mixture is allowed to warm up slowly to room temperature and stirred for 12 hours at that temperature. Dicyclohexylurea is filtered, and the filtrate evaporated under reduced pressure. The residue is dissolved in ethyl acetate, washed successively with cold 1N HCl, 1N NaOH and dried over anhydrous $MgSO_4$. The amide is purified by column chromatography (silica gel, EtOAc/cyclohexane; 1:1, Rf 0.22 (EtOAc/cyclohexane, 1:1).

EXAMPLE 35

4-Amino 2,2-difluoro 3-hydroxy N-(isoamylaminocarbonyl-ethyl) 6-methyl-heptanamide hydrochloride 4-N-tert-Butoxycarbonylamino 2,2-difluoro 3-hydroxy N-1-isoamylaminocarbonylethyl)-6-methyl heptanamide (0.457 g) is dissolved in a solution of about 4N HCl in diethylether (5 ml) and stirred at room temperature for 14 hours. Afterthe removal of excess reagent under reduced pressure, the solid residue was triturated with ether to form a solid which is dried, in vacuo for 8 hours. Rf 0.63 (AcOH/butanol/$H_2O$; 2:6:2).

EXAMPLE 36

4-[(2-N-isovaleryl-3-methyl-1-oxobutyl)amino]2,2-difluoro 3-hydroxy-N-( 1-isoamylaminocarbonylethyl) 6-methyl heptanamide To a solution of 0.130g (0.33 mmol) of 4-amino 2,2-difluoro 3-hydroxy N-(1-isoamylaminocarbonylethyl) 6-methyl-heptanamide HCl in THF (10 ml) is added 0.034 g (0.33 mmol) of N-methyl morpholine at room temperature. After 10 min., the mixture is cooled to 0° C.; a solution of 0.103 g (0.50 mmol) of DCC in THF (1 ml) is then added, followed by the addition of 0.100 g (0.50 mmol) of N-isovaleryl valine. Stirring is continued for 15 hours, while the temperature is allowed to rise to room temperature. The precipitate is filtered off and the filtrate rinsed with THF. The Solvent is evaporated in vacuo; the residue is purified by chromatography (silica gel, $CH_3OH/CHCl_3$ 2:98) yielding 0.06 g of the expected amide. Rf: 0.45 ($CH_3OH/CHCl_3$ 8:92).

EXAMPLE 37

4-[(2-N-isovalerylamino-3-methyl-1-oxobutyl)amino]2,2-difluoro-N-(1-isoamylaminocarbonylethyl) 6-methyl 3-oxo heptanamide A solution of 0.214 g (0.40 mmol) of 4-[2-N-isovalerylamino- 3-methyl-1-oxobutyl)amino] 2,2-difluoro 3-hydroxy-N-(1-isoamylaminocarbonylethyl) 6-methyl heptanamide in $CH_2Cl_2$ (4 ml) is added to a suspension of pyridinium dichromate (0.228 g) and 3° Angstroms molecular sieves (0.336 g), containing 20 microliter of glacial acetic acid. Stirring is continued for 15 hours at room temperature. Florisil (0.200 g) is added, stirring continued for 0.25 hours and the mixture filtered. Removal of the solvent and chromatography (silica gel, ethyl acetate/acetone 7:3) afford the expected ketone. Rf: 0.3 (ethyl acetate/chloroform 1:1).

EXAMPLE 38

4-N-tert-butoxycarbonylamino 2,2-difluoro 6-methyl 3-oxo heptanoic acid, ethyl ester The title compound was prepared in 65% yield from the alcohol described in example 32 by the preceding procedure. The ketone was purified by chromatography (silica gel, ethyl acetate/cyclohexane 1:9).

EXAMPLE 39

4-amino 2,2-difluoro 6-methyl 3-oxo heptanoic acid, ethyl ester hydrochloride

The BOC protecting group of the ketone of example 38 is cleaved using the same procedure as for the amide described in example 35. m.p: 127°–128° C. (decomp).

EXAMPLE 40

Ethyl-3-keto-2-methyl-4,4,4-trifluorobutanoate

Sodium hydride (7.05 g of a 50% oil dispersion, 0.15 mol) was washed 3 times with 25 ml of dimethoxyethane to remove the oil and then suspended in 220 ml of dimethoxyethane, under an argon atmosphere and cooled in an ice bath. A solution of ethyl 3-keto-4,4,4-trifluorobutanoate (25.77 g, 0.14 mol) in 25 ml of dimethoxyethane was added dropwise from an addition funnel to the stirred suspension. After the addition was completed, the cooling bath was removed and the reaction mixture stirred for 30 minutes past the cessation of hydrogen gas evolution. Methyl iodide (43.0 ml, 0.70 mole) was added by syringe and the reaction mixture refluxed overnight. The reaction was cooled to room temperature and poured into a separatory funnel containing a 1:1:1 mixture of saturated ammonium chloride:brine:water. The layers were separated and the aqueous phase extracted with 100 ml ether. The combined organic phase and ether extract was washed with brine, dried over magnesium sulfate and filtered. The solvents were removed by distillation at atmospheric pressure using a Vigreaux column leaving ethyl 3-keto-2-methyl-4,4,4-trifluorobutanoate as the pot residue. Rf: (EtAc/hexane—20:80)

EXAMPLE 41

Ethyl 3-hydroxy-2-methyl-4,4,4-trifluorobutanoate

To a solution of ethyl 3-keto-2-methyl-4,4,4-trifluorobutanoate (20.1 g, 0.10 moles) in 250 ml of absolute ethanol, cooled in an ice bath, was added sodium borohydride (1.0 g, 0.25 moles) in portions with stirring. The cooling bath was removed and the reaction stirred at room temperature for 30 minutes. Acetone (5 ml) was added to quench any remaining sodium borohydride and the solvents removed by distillation at atmospheric pressure using a Vigreaux column. The residue was diluted with 200 ml of methylene chloride and poured into a separatory funnel containing 75 ml of a 1:1:1 mixture of saturated ammonium chloride:brine:water. The layers were separated and the aqueous phase extracted with methylene chloride (3×25 ml). The combined organic phase and methylene chloride extracts were dried over magnesium sulfate, filtered and distilled at atmospheric pressure to remove the solvents. The residue was then distilled at reduced pressure (20 mmHg) using a Vigreaux column to give ethyl 3-hydroxy-2-methyl-4,4,4-trifluorobutanoate, bp 78°–84° C., 20 mmHg.

EXAMPLE 42

3-Hydroxy-2-methyl-4,4,4-trifluorobutanamide

Into a solution of ethyl 3-hydroxy-2-methyl-4,4,4-trifluorobutanoate (11.4 g, 51.0 mmol) in 85 ml of methanol, cooled in an ice bath, was bubbled in anhydrous ammonia forseveral minutes. The reaction flask was sealed with a septum and stirred at room temperature for 6 days. The mixture was concentrated using a rotary evaporator and the residue distilled at reduced pressure using a vacuum pump to remove all components with a boiling point less than 25° C. at 0.05 mmHg leaving trifluorobutanamide (5.8 g, 33.9 mmol) as the pot residue.

EXAMPLE 43

3-Hydroxy-4,4,4-trifluoro-2-butylamine hydrochloride

To potassium hydroxide pellets (15.4 g of 85% pellets, 0.23 moles) dissolved in 45 ml of water and cooled in an ice bath was added bromine (2.7 ml, 51.4 mmol). After several minutes, a solution of 3-hydroxy-2-methyl-4,4,4-trifluorobutanamide (8.0 g, 46.8 mmol) in 45 ml water, pre-cooled in an ice bath, was added. The reaction was stirred at ice bath temperatures for 20 minutes and then at room temperature for 30 minutes. Finally, the reaction was heated on a steam bath for 30 minutes. The reaction mixture was cooled to room temperature and poured into a separatory funnel where it was extracted with methylene chloride (3×50 ml). The aqueous layer was then saturated with solid sodium chloride and extracted further with two portions of methylene chloride (25 ml). The combined organic extracts were dried over magnesium sulfate, filtered and the solvent removed at ambient temperature on a rotary evaporator. The residue was dissolved in anhydrous ether (250 ml) and anhydrous hydrogen chloride gas bubbled through the reaction mixture. A white precipitate formed and the suspension was cooled in an ice bath. The precipitate was filtered and then recrystallized from acetone ether to give 3-hydroxy-4,4,4-trifluoro-2-butylamine hydrochloride, Rf: 0.25 ($NH_4OH/CH_3OH/CH_2Cl_2$—2:10:88).

EXAMPLE 44

L-Alanine methyl ester hydrochloride

To a suspension of L-alanine (25.0 g, 0.28 moles) in 125 ml of methanol, cooled in an ice-methanol bath, was added thionyl chloride (21.0 ml, 0.29 moles) dropwise at a rate such that the internal reaction temperature was main-tained at 5° C. or less. After the addition was completed, the cooling bath was removed and the reaction mixture warmed to 45° C. for 2 hours. The reaction mixture was filtered to remove a small amount of yellow solid and the filtrate concentrated using a rotary evaporator. To the resultant oil was added tetrahydrofuran (50 ml) and the mixture evaporated to dryness on a rotary evaporator. The residue was placed under high vacuum to yield an off white solid. Ether (300 ml) was added to the solid and the suspension digested on a steam bath. Cooling and filtering gave L-alanine methyl ester hydrochloride (37.2 g, 0.26 mmol).

EXAMPLE 45

Boc-L-Alanine methyl ester

To a stirred suspension of L-alanine methyl ester hydrochloride (10.0 g, 71.6 mmol) in methylene chloride (220 ml) under an argon atmosphere was added triethylamine (10.0 ml, 71.6 mmol). Fifteen minutes later, a solution of di-tert-butyl dicarbonate (15.3 g, 70.2 mmol) in methylene chloride (30 ml) was added dropwise. After the addition was complete, the reaction mixture was stirred at room temperature overnight. The reaction mixture was poured into a separatory funnel containing 50 ml water and the layers separated. The organic layer was washed with 0.5N hydrochloric acid (2×50 ml) and brine (50 ml). The organic layer was then dried over magnesium sulfate, filtered and the majority of solvent evaporated using a rotary evaporator. The last traces of solvent were removed under high vacuum to give Boc-L-alanine methyl ester (14.27 g, 70.2 mmol).

EXAMPLE 46

Boc-L-Alaninal

Boc-L-alanine methyl ester (5.0 g, 24.6 mmol) was dissolved in dry toluene (150 ml) under an argon atmosphere-and cooled in a dry ice-acetone bath. To this vigorously stirred solution was added a solution of diisobutylaluminumhydride (1.0M in hexanes, 61.5 ml, 61.5 mmol), pre-cooled in a dry ice-acetone bath, via a transfer needle. After 6 minutes, the reaction was carefully quenched with methanol (4 ml) and the mixture allowed to warm to room temperature. The reaction mixture was poured into a separatory funnel containing 250 ml ether and 200 ml of ice cold 0.25N hydrochloric acid. The layers were separated and the organic layer was washed with 0.25N hydrochloric acid (3×80 ml) and brine (50 ml). The organic layer was dried overmagnesium sulfate, filtered and concentrated using a rotary evaporator at ambient temperature. The residue was chromatographed using hexanes—30% ethylacetate to give Boc-L-alaninal. The compound may also be prepared by the technique described in Synthesis, 1983, pg. 676.

EXAMPLE 47

(3S)-3-Amino-2-hydroxybutanoic acid

To a suspension of Boc-L-alaninal (2.5 g, 14.4 mmol) in ice cold water (30 ml) was added an ice cold solution ofsodium bisulfite (1.5 g, 14.4 mmol) in water (10 ml). The resultant suspension was stirred at ice bath temperature overnight. To the resultant solution was added ethyl acetate (200 ml) and then a solution of potassium cyanide (0.9 g, 14.4 mmol) in water (10 ml). The reaction mixture was stirred at room temperature for 4 hours and then pouredinto a separatory funnel and the layers separated. The organic layer was washed with water (2×100 ml) and brine (75 ml), then dried over magnesium sulfate, filtered and concentrated using a rotary evaporator. The cyanohydrin was dissolved in dioxane (50 ml) and concentrated hydro-chloric acid (50 ml) added. The reaction mixture was refluxed overnight and then cooled to room temperature. The reaction mixture was poured into a separatory funnel containing ether (100 ml) and the layers separated. The aqueous layer was extracted with a further 100 ml ether and then evaporated to dryness on a rotary evaporator. The resultant residue was dissolved in water (30 ml) and the pHadjusted to approximately 7 with 2N ammonium hydroxide. This solution was placed on a Biorad AG 50 W-X8 H⊕ resin column and eluted with 2N ammonium hydroxide. Combination of the appropriate fractions and evaporation gave crude (3S)-3-amino-2-hydroxybutanoic acid which was then recrystallized from water-acetone to give the desired product (1.05 g, 8.8 mmol) as a white solid.

EXAMPLE 48

Methyl (3S)-3-amino-2-hydroxybutanoate

Into a suspension of (3S)-3-amino-2-hydroxybutanoic acid (1.0 g, 8.4 mmol) in methanol (25 ml) was bubbled anhydrous hydrogen chloride gas until a solution resulted. After a solution resulted, the reaction was cooled in an ice bath and saturated with hydrogen chloride. The cooling bath was removed and the reaction stirred at room temperature for 3.5 hours. The solvent was removed on a rotary evaporator at ambient temperature and the resultant residue dissolved in methanol (25 ml), cooled in an ice bath and saturated with hydrogen chloride gas. Warming of the reaction solution to room temperature and removal of the solvent on a rotary evaporator gave an oil. To this oil was added triethylamine (15 ml) followed by the minimum amount of methanol (about 15 ml) needed to dissolve the initial gummy solid. The solution was cooled in an ice bath and ether (75 ml) added in portions with stirring. The precipitated triethylamine hydrochloride was filtered and the filtrate evaporated to give methyl (3S)-3-amino-2-hydroxybutanoate.

EXAMPLE 49

Boc-L-alanyl-L-proline benzyl ester

Boc-L-alanine (19.5 g, 0.10 mol) was dissolved in dry tetrahydrofuran (90 ml) under an argon atmosphere in a flask fitted with an overhead stirrer and an internal thermometer. The solution was cooled to −15° C. and N-methylmorpholine (11.4 ml, 0.10 mol) was added followed by isobutylchloroformate (13.4 ml, 0.10 mol) at such a rate as to maintain the internal reaction temperature at −10° to −15° C. Five minutes after the addition was completed, a solution of L-proline benzyl ester hydrochloride (25.2 g, 0.10 mol) and N-methylmorpholine (11.4 ml, 0.10 mol) in chloroform (90 ml) was added dropwise at such a rate as to maintain the internal reaction temperature at −10° to −15° C. After the addition was completed, the reaction mixture was allowed to slowly warm to room temperature and then stirred at room temperature overnight. The reaction mixture was concentrated using a rotary evaporator, the residue diluted with ethyl acetate (500 ml)/0.2N hydrochloric acid (100 ml) and poured into a separatory funnel. The layers were separated and the aqueous phase extracted with a further 150 ml ethyl acetate. The combined organics were washed with 0.2N hydrochloric acid (2×100 ml), water (100 ml), saturated sodium bicarbonate (2×100 ml), again with water (100 ml) and finally brine (100 ml). The organic phase was dried over magnesium sulfate, filtered and concentrated on a rotary evaporator. Chromatography using ethyl acetate-hexane as the eluent gave Boc-L-alanyl-L-proline benzyl ester, Rf: 0.15 (EtOAc/hexane—30:70).

EXAMPLE 50

L-Alanyl-L-proline benzyl ester hydrochloride

Into a solution of Boc-L-alanyl-L-proline benzyl ester (31.6 g, 83.94 mmol) in ethyl acetate (400 ml) cooled in an ice bath was bubbled hydrogen chloride gas for 15 minutes. The addition of gas was ceased, the cooling bath removed and the solution stirred at room temperature for 1.5 hours. Concentration using a rotary evaporator followed by drying the residue [in a vacuum desiccator over potassium hydroxide pellets overnight] gave L-alanyl-L-proline benzylester hydrochloride (25.5 g, 81.5 mmol).

EXAMPLE 51

Boc-L-alanyl-L-alanyl-L-proline benzyl ester

L-alanyl-L-proline benzyl ester hydrochloride (13.0 g,41.6 mmol) was dissolved in methylene chloride (650 ml) under an argon atmosphere in a flask fitted with an over-head stirrer. N-methylmorpholine (4.8 ml, 43.6 mmol) was syringed into the solution and, after 5 minutes, Boc-L-alanine (7.9 g, 41.6 mmol) was added followed by 1-ethoxycarbonyl-2-ethoxy-1,2-dihydroquinoline (11.8 g, 47.8 mmol). The resulting solution was stirred at room temperature overnight. The reaction mixture was poured into a separatory funnel containing water (300 ml) and the layers separated. The aqueous layer was extracted with chloroform (200 ml) and the combined organic extracts were washed with0.5N hydrochloric acid (3×200 ml), water (2×200 ml), saturated sodium bicarbonate (2×200 ml) and brine (200 ml). The organic layer was then dried over magnesium sulfate, filtered and concentrated on a rotary evaporator. Addition of ether-hexane gave crude Boc-L-alanyl-L-alanyl-L-proline benzyl ester which could be recrystallized from ethyl acetate-hexane to give the pure product (15.1 g) mp 124°–126° C.

EXAMPLE 52

L-Alanyl-L-alanyl-L-proline benzyl ester hydrochloride

Into a solution of Boc-L-alanyl-L-alanyl-L-proline benzyl ester (25.5 g, 57.0 mmol) in ethyl acetate (650 ml) cooled in an ice bath was bubbled hydrogen chloride gas for 15 minutes at which time bubbling was ceased. The cooling bath was removed and the solution stirred at room temperature for 1.5 hours. The reaction mixture was concentrated on a rotary evaporator and the resultant gummy solid dissolved in methylene chloridehexane. Removal of the solvents gave L-alanyl-L-alanyl-L-proline benzyl ester hydrochloride which was dried over potassium hydroxide pellets in a vacuum desiccator overnight to yield 21.09 (54.7 mmol) of the desired product.

EXAMPLE 53

Methoxysuccinyl-L-alanyl-L-alanyl-L-proline benzyl ester

To a solution of L-alanyl-L-alanyl-L-proline benzyl ester hydrochloride (19.2 g, 50.0 mmol), mono-methyl succinate (6.6 g, 50.0 mmol) and 1-hydroxybenzotriazole.x$H_2O$ (16.9 g) in N,N-dimethylformamide (125 ml) under an argon atmosphere and cooled in an ice bath was added N-methylmorpholine (5.5 ml, 50.0 mmol). After 5 minutes, N,N'-dicyclohexylcarbodiimide (11.9 g, 57.5 mmol) was added, the cooling bath removed and the reaction mixture stirred at room temperature overnight. The reaction mixture was filtered and the filtrate poured into a separatory funnel containing chloroform (750 ml)/0.5N hydrochloric acid (250 ml). The layers were separated and the aqueous phase extracted with chloroform (200 ml). The combined organic extracts were washed with 0.5N hydrochloric acid (2×250 ml), water (2×250 ml), saturated sodium bicar-bonate (2×250 ml) and brine (250 ml). The organic layer was dried over magnesium sulfate, filtered and concentrated on a rotary evaporator. The last traces of solvent were removed using a vacuum pump and the residue chromatographed using acetone-ethyl acetate as the eluent. The resultant crude MeOSuc-L-alanyl-L-alanyl-L-proline benzyl ester was recrystallized from ethyl acetate to give pure product m.p. 124°–127° C.

EXAMPLE 54

MeOSuc-L-alanyl-L-alanyl-L-proline

Into a Parr flask flushed with argon containing 4.0 g of 10% palladium on charcoal catalyst was added tert-butanol (775 ml) and then MeOSuc-L-alanyl-L-alanyl-L-pro-line benzyl ester (13.0 g, 28.2 mmols). The mixture was shaken under 30 psi of hydrogen at 30°–40° C. overnight. The mixture was filtered through celite and the filtrate concentrated on a rotary evaporator. The residue, was azeotroped with chloroform-hexane to remove the last traces of tert-butanol and then dried under high vacuum to give MeOSuc-L-alanyl-L-alanyl-L-proline (10.4 g, 28.0 mmol).

EXAMPLE 55

Acetyl-L-prolyl-L-alanyl-L-proline benzyl ester

Ac-L-proline (3.05 g, 19.41 mmol) was dissolved in drytetrahydrofuran (100 ml) under an argon atmosphere in a flask fitted with an overhead stirrer and an internal thermometer. The solution was cooled to −15° C. and N-methylmorpholine (2.13 ml, 19.41 mmol) was added followed by isobutylchloroformate (2.51 ml, 19.41 mmol) at such a rate as to maintain the internal reaction temperature at −10° to −15° C. Five minutes after the addition was completed, a solution of L-alanyl-L-proline benzyl ester hydrochloride (6.08 g, 19.41 mmol) in chloroform (70 ml) was added followed by a second portion of N-methylmorpholine (2.13 ml, 19.41 mmol) at such a rate as to maintain the internal reaction temperature at −10° to −15° C. The reaction mixture was then allowed to slowly warm to room temperatureand stirred at room temperature for 2.5 hours. Thereaction mixture was concentrated to a small residue on a rotary evaporator, diluted with chloroform (500 ml) and poured into a separatory funnel where it was washed with 0.2N hydrochloric acid (3×200 ml) and 5% sodium bicarbonate (200 ml). The organic layer was dried over magnesium sulfate, filtered, concentrated on a rotary evaporator and chromatographed using methylene chloride-methanol as an eluent to give Ac-L-prolyl-L-alanyl-L-proline benzyl ester; Rf: 0.35 ($CH_3OH/CH_2Cl_2$—7:93).

EXAMPLE 56

Acetyl-L-prolyl-L-alanyl-L-proline

Into a Parr flask flushed with argon containing 450 mg of 10% palladium on charcoal catalyst was added a solution of Ac-L-prolyl-L-alanyl-L-proline benzyl ester in (1.0 g, 2.41 mmol) absolute ethanol (100 ml). The contents were shaken under 40 psi of hydrogen overnight at room temperature. The mixture was filtered through celite and the filtrate concentrated on a rotary evaporator to give crude Ac-L-prolyl-L-alanyl-L-proline which was crystallizedfrom tetrahydrofuran-methanol-ether to give the desired product (0.57 g) in 73% yield.

EXAMPLE 57

1,1,1-Trifluoro-3-[(N-acetylprolyl)alanylprolylamino]butan-2-ol

Ac-L-prolyl-L-alanyl-L-proline (1.17 g, 3.61 mmol) was suspended in dry acetonitrile (55 ml) under an argon atmosphere in a flask fitted with an overhead stirrer and internal thermometer. The suspension was cooled to −15° C. and N-methylmorpholine (0.40 ml, 3.61 mmol) was added followed by isobutylchloroformate (0.47 ml, 3.61 mmol) at such a rate as to maintain the internal reaction temperature at −10° to −15° C. Ten minutes after the addition was completed, a mixture of 3-hydroxy-4,4,4-trifluoro-2-butylamine hydrochloride (0.65 g, 3.61 mmol) and N-methylmorpho-line (0.40 ml, 3.61 mmol) in chloroform (25 ml) was added at such a rate as to maintain the internal reactiontemperature at −10° to −15° C. The reaction mixture was allowed to warm slowly to room temperature and then stirred at room temperature for 4 hours. The reaction mixture was evaporated on a rotary evaporator to an oily residue which was dissolved in water (65 ml) and treated with a mixed bed resin (J. T. Baker—ANGMI-615, 17 g). After 15 minutes the mixture was filtered and the filtrate evaporated on a rotary evaporator. Chromatography using methylene chloride—10% methanol as the eluent gave the above-named product, (0.37 g) in 23% yield.

EXAMPLE 58

1,1,1-Trifluoro-3-[(N-acetylprolyl)alanylprolylamino]-butane-2,2-diol

To a solution of oxalyl chloride (72 μl, 0.83 mmol) in methylene chloride (1 ml) under an argon atmosphere and cooled in a dry ice-acetone bath was added dimethylsulfoxide (0.12 ml, 1.65 mmol) with stirring. After 5 minutes, a solution of the compound of example 57 (0.25 g, 0.55 mmol) in methylene chloride (1.5 ml) was added. The reaction mixture was stirred for 15 minutes, triethylamine (0.50 ml,3.58 mmol) then added and the reaction warmed to room temperature for 30 minutes. The reaction mixture was placed directly onto a silica gel column and eluted with methylene chloride-methanol. Trituration of the resultant oily solid with ether-hexane and filtration gave the above-named product, (50 mg, 0.11 mmol).

EXAMPLE 59

3-[(N-acetylprolyl)alanylprolylamino]-2-hydroxybutanoic acid, methyl ester

Ac-L-prolyl-L-alanyl-L-proline (0.65 g, 2.00 mmol) wassuspended in dry acetonitrile (20 ml) under an argon atmosphere in a flask fitted with an overhead stirrer and internal thermometer. The suspension was cooled to −15° C. and N-methylmorpholine (0.22 ml, 2.00 mmol) was added followed by isobutylchloroformate (0.26 ml, 2.00 mmol) at such a rate as to maintain the internal reaction temperature at −10° to −15° C. After 10 minutes, a solution of methyl (3S)-3-amino-2-hydroxybutanoate (0.53 g, 4.00 mmol) in chloroform (2.5 ml) was added at such a rate as to maintain the internal reaction temperature at −10° to −15° C. The reaction mixture was slowly warmed to room temperature and then stirred for 3 hours. The reaction mixture was evaporated on a rotary evaporator, the residue dissolved in water (20 ml) and treated with a mixed bed resin (J. T. Baker—ANGMI-615, 11.0 g). After 15 minutes the mixture was filtered and the filtrate evaporated on a rotary evaporator. Chromatography using methylene chloride-methanol as the eluent gave the above-named product (0.32 g) in 36% yield.

EXAMPLE 60

3-[(N-acetylprolyl)alanylprolylamino]-2,2-dihydroxybutanoic-acid, methyl ester

To a stirred solution of oxalyl chloride (0.12 ml, 1.43 mmol) in methylene chloride (1.5 ml) under an argon atmosphere and cooled in a dry ice-acetone bath was added dropwise a solution of dimethylsulfoxide (0.20 ml, 2.86 mmol) in methylene chloride (1.5 ml). After 5 minutes, a solution of the product of example 59 (0.32 g, 0.72 mmol) in methylene chloride (1.5 ml) was added and the reaction mixture stirred for 25 minutes. Triethylamine (0.50 ml, 3.58 mmol) was added and the reaction mixture warmed to room temperature. The reaction mixture was placed directly onto a silica gel column and eluted with methylene chloride-methanol. Evaporation of the appropriate fractions on a rotary evaporator, addition of water (3 ml) to the residue and evaporation gave the above-namedproduct.

EXAMPLE 61

{N-acetylprolyl)alanylprolylamino]-2,2-dihydroxybutanoic acid

To a solution of the product of example 60 (0.10 g, 0.23 mmol) in water (4 ml) cooled in an ice bath was added 1N lithium hydroxide (0.50 ml of an aqueous solution, 0.50 mmol). After 1 hour the pH of the reaction mixture was adjusted to 4.5 to 5.0 with 1N hydrochloric acid and the reaction evaporated on a rotary evaporator. The residue was chromatographed using methylene chloride-methanol as the eluent. Evaporation of the appropriate fractions, addition of water (2 ml) to the residue and evaporation gave the above-named product (65 mg) in 64% yield.

EXAMPLE 62

Boc-L-alanyl-L-alanyl-L-proline

A Parr flask was flushed with argon and charged with 10% palladium on charcoal (0.74 g), followed by the addition of Boc-L-alanyl-L-alanyl-L-proline benzyl ester (1.8 g, 4.0 mmol) dissolved in tert-butanol (300 ml). The reaction mixture shaken under 30 psi of hydrogen at 35° C. for 5 hr. After cooling to room temperature, ethanol (50 ml) was added and the solution was filtered through celite and the filtrate concentrated on a rotary evaporator. The residue was azeotroped with chloroform-hexane to remove the last traces of tert-butanol and then dried under high vacuum to give Boc-L-alanyl-L-alanyl-L-proline (1.40 g, 3.9 mmol) in 98% yield.

EXAMPLE 63

1,1,1-Trifluoro-3-[(N-tert-butyloxycarbonylalanyl)alanylprolylamino]-4-methylpentan-2-ol To a solution of Boc-L-alanyl-L-alanyl-L-proline (1.0 g, 2.80 mmol) in dry acetonitrile (25 ml) was added N-methylmorpholine (0.34 ml, 3.06 mmol). The solution was cooled to −20° C. and isobutylchloroformate (0.37 ml, 2.88 mmol) was added dropwise. To this solution, a pre-cooled (−20° C.) mixture of 3-amino-1,1,1-trifluoro-4-methyl-2-pentanol hydrochloride (0.61 g, 2.91 mmol), N,N-dimethylformamide (4ml) and N-methylmorpholine (0.34, 3.06 mmol) was added. The reaction mixture was stirred at −20° C. for 4 hr, allowed to warm to room temperature and stirred overnight. Removal of the solvents in vacuo produced a pale yellow residue, which was purified by flash chromatography using ethyl acetate as an eluent to give 1,1,1-Trifluoro-3-[(N-tert-butyloxycarbonylalanyl)alanylprolylamino]-4-methylpentane-2-ol (1.09 g, 2.1 mmol) in 76% yield.

EXAMPLE 64

1,1,1-trifluoro-3-[N-tert-butyloxycarbonylalanyl)alanylprolylamino]-4-methylpentan-2-one A solution of oxalyl chloride (0.078 ml, 0.9 mmol) in methylene chloride (2 ml) was cooled to −55° C. and dimethylsulfoxide (0.125 ml, 1.8 mmol) was added dropwise. The solution was stirred for 5 min, followed by the addition of 1,1,1-trifluoro-3-[N-tert-butyloxycarbonylalanyl)alanylprolylamino]-4-methylpentan-2-ol (260 mg, 0.53 mmol) in methylene chloride (1.5 ml). The mixture was stirred for 15 min and triethylamine (0.45 ml, 3.2 mmol) was added. The reaction mixture was allowed to warm to room temperature, the solvent was removed in vacuo and the crude product was loaded directly onto a silica gel column (230–400 mesh) for purification. Elution with ethyl acetate gave 1,1,1-trifluoro- 3-[N-tert-butyloxycarbonylalanyl)alanylprolylamino]-4-methylpentan-2-one (180 mg, 0.37 mmol) in 70% yield.

EXAMPLE 65

1,1,1-Trifluoro-3-[alanyl-alanylprolylamino]-4-methylpentan-2-one

A solution of 1,1,1-Trifluoro-3[(N-tert-butyloxycarbonylalanyl)alanyl-prolylamino]- 4-methylpentan-2-one (180 mg, 0.35 mmol) in ethyl acetate (50 ml) was cooled to 0° C. and treated with hydrogen chloride gas for 5 min. The reaction mixture was stirred at 0° C. for 1.5 hr, followed by removal of solvent in vacuo. 1,1,1-Trifluoro-3-[alanylalanylprolylamino]-4-methylpentan-2-one (151 mg, 0.34 mmol) was obtained in 96% yield and was used for subsequent reactions without purification.

EXAMPLE 66

Dansyl peptide 1,1,1-Trifluoro-3-(alanylalanylprolyamino)-4-methylpentan-2-one

To a suspension of 1,1,1-Trifluoro-3-(alanylalanylprolylamino)-4-methylpentan-2-one (50 mg, 0.11mmol) in methylene chloride (1 ml), was added N-methylmorpholine (50 mg, 0.5 mmol). The solution was stirred for 5 min and dansyl chloride (50 mg) then added. The reaction mixture was stirred for 2 h at room temperature with the exclusion of light and then loaded directly onto a silica gel column (230-400 mesh) for purification. Elution with ethylacetate gave the dansylated peptide (48 mg, 0.07 mmol) in 68% yield.

EXAMPLE 67

$N^1$-(2-Methoxyethoxymethoxy-3,3-difluoro-1-isobutyl-5-hexenyl-$N^2$-isovaleryl valinamide To 0.211 g of sodium hydride (55%, 4.83 mmol) in 3 ml of DMF at 0° C. was added 1.8 g (4.6 mmol) of $N^1$-(2-hydroxy-3,3-difluoro-1-isobutyl- 5-hexenyl)-$N^2$-isovaleryl valinamide, in 5 ml of DMF. After stirring OKC for 10 min., methoxyethoxymethylchloride (0.659 g, 5.29 mmol in 3 ml DMF) was added, the mixture stirred for 10 min. at 0° C. and overnight at room temperature. Workup with water/$Et_2O$ gave, after purification by flash chromatography ($CHCl_3$/$Et_2O$, 2:1) 1.4 g of the desired product.

EXAMPLE 68

$N^1$-(2-Methoxyethoxymethoxy-3,3-difluoro-1-isobutyl-4-carboxybutyl)-$N^2$-isovaleryl valinamide The above-named compound was prepared from $N^1$-2-methoxyethoxymethoxy-3,3-difluoro-1-isobutyl- 5-hexenyl)-$N^2$-isovaleryl valinamide by the procedure described in example 8 using equivalent proportions and conditions.

EXAMPLE 69

$N^1$-(2-Methoxyethoxymethoxy-3,3-difluoro-1-isobutyl-4-[ 1-(Isoamylaminocarbonyl)ethyl]methylaminocarbonylbutyl)-$N^2$-isovaleryl valinamide The above-named compound was prepared from $N^1$-(2-mehoxyethoxymethoxy-3,3-difluoro- 1-isobutyl-4-carboxybutyl)-$N^2$-isovaleryl valinamide by the procedure described in example 49. Proportions: 1.50 g (3.02 mmol) peptide acid in 10 ml THF, 0.306 g (0.33 ml, 3.02 mmol) N-methyl morpholine, 0.412 g (3.02 mmol) isobutylchloroformate, N-methyl alanine isoamylamide hydrochloride (0.63 g, 3.02 mmol) and N-methyl morpholine (0.306 g, 3.02 mmol) in 5 ml THF. Flashchromatography (EtOAc/Pentane, 2:1) gives 0.3 g of the above-named compound. From 1.50 g of the peptide acid, using the procedure of example 49 there is produced, after purification by flash chromatography, 0.39 g of the desiredproduct.

EXAMPLE 70

$N^1$-(2-Hydroxy-3,3-difluoro-1-isobutyl-4[[ 1-(isoamylaminocarbonyl)ethyl]-methylamino] carbonylvutyl)-$N^2$-isovaleryl valinamide A mixture of 0.3 g (0.46 mmol) of $N^1$-(2-methoxyethoxymethoxy-3,3-difluoro-1-isobutyl- 4-[[1-(isoamylaminocarbonyl) ethyl]-methylamine]carbonylbutyl)-$N^2$-isovaleryl valinamide and 0.52 g (2.31 mmol) of $ZnBr_2$ in 3 ml $CH_2Cl_2$ was stirred for 24 h at room temperature. Flash chromatography (EtOAc) gives 0.11 g of the above-named alochol.

EXAMPLE 71

$N^1$-(2-Oxo-3,3-difluoro-1-isobutyl-4[[1-(isoamylamino)ethyl]methylamino]carbonylbutyl)-N 2-isovaleryl valinamide The above-named compound was prepared from $N^1$-(2-Hydroxy-3,3-difluoro- 1-isobutyl-4[[1-(isoamylamino)ethyl]methylamino]carbonylbutyl)-$N^2$-isovaleryl valinamide by the procedure described in example 7. Proportions: Oxalylchloride (0.176 mmol, 0.0224 mg) in 0.5 ml $CH_2Cl_2$, 0.0275 mg (0.352 mmol) DMSO, 90 mg of alcohol in 1.5 ml $CH_2Cl_2$ (at −55° C.), 0.081 g $Et_3N$ (0.8 mmol). Flash chromatography (EtOAc) gave 0.02 g of above-named compound.

EXAMPLE 72

4-N-tert-butoxycarbonylamino 2,2-difluoro 3-hydroxy 5-methyl hexanoic acid, ethyl ester The title compound was prepared in 35% yild from L-BOC valinal using the same procedure as for the ester, described in example 32. Rf=0.52 (EtOAc/$C_6H_{12}$ 1:1)

EXAMPLE 73

4-Amino 2,2-difluoro 3-hydroxy 5-methyl hexanoic acid, ethyl ester hydrochloride The Boc protecting group of the alcohol of example 72 is cleaved using the same procedure as for the amide described in example 35, mp 182° C.

EXAMPLE 74

4-[methoxysuccinyl L-alanyl-L-alanyl-L-prolyl]amino 2,2-difluoro 3-hydroxy 5-methyl hexenoic acid, ethyl ester To a stirred solution of 0.371 g (1 mmol) of MeOSuc-L-Ala-L-Ala-L-ProOH in dry acetonitrile (10 ml) under nitrogen was added 0.106 g (1.05 mmol) of N-methyl-morpholine. The resultant solution was cooled to −20° C. Isobutyl chloroformate (0.136 g, 1 mmol) was added to the cooled reaction mixture. After 10 min. a solution of 0.275 g (1.05 mmol) of 4-amino 2,2-difluoro 3-hydroxy 5-methyl hexanoic acid, ethyl ester hydrochloride and 0.106 g (1.05 mmol) of N-methylmorpholine in dry DMF (2 ml) was added to the cooled mixture. The reaction mixture was stirred at −20° C. for 4 hours and then allowed to warm to room temperature. After stirring 15 hours at room temperature the mixture is concentrated and placed under high vacuum at 40° C. to remove all the DMF. Chromatography (silica gel, ethyl acetate/acetone 7:3) yielded the expected alcohol in 85% yield. Rf: 0.38 (ethyl acetate/acetone 1:1).

EXAMPLE 75

4-[Methoxysuccinyl-L-alanyl-L-alanyl-L-prolyl]amino 2,2-difluoro 5-methyl 3-oxo hexanoic acid, ethyl ester The title compound was obtained in 65% yield from the alcohol of example 74 using the procedure described in example 37, mp: 96°–97° C.

The foregoing describes in detail the generic and specific aspects of the scope of the invention as well as the manner of making and using the invention. In addition thereto, although such procedures are known in the art, references setting forth state of art procedures by which the compounds may be evaluated for their biochemical effects is also included herein.

For example, human elastase is assayed in vitro using chromophoric peptides, succinylalanylalanylalanyl-p-nitroanilide (A1), methoxysuccinylalanylalanylprolylvalyl-pnitroanilide (A2), and others, all of which are available commercially. The assay buffer, pH 8.0, and assay techniques are similar to those described by Lottenberg et al. (A3, A4). Enzyme is purified from human sputum (A5), although recently it has become commercially available. Kinetic characterization of immediate inhibitors is by means of the Dixon plot (A6), whereas the characterization of slow-and/or tight-binding inhibitors used data analysistechniques reviewed by Williams and Morrison (A7).

Similarly, the other proteases are assayed and effects of inhibitors are assessed in vitro by similar spectro-scopic techniques: cathepsin G (A2); thrombin (A3); chymotrypsin (A8); trypsin (A9); plasmin (A3); $C_1$ esterase (A10); urokinase (A3); plasminogen activator (All); acrosin(A12); beta-lactamase (A13); cathepsin B (A14); pepsin (A15); cathepsin D (A16) and leucine aminopeptidase (A17). Pseudomonas elastase is measured in a coupled assay procedure using a human elastase substrate and microsomal aminopeptidase.

Radiometric assays of angiotensin I-converting enzyme and enkephalinase and their inhibitors are based on the procedure of Ryan (A18) and use tritiated substrate purchased from Ventrex Laboratories, Inc. Radioimmunoassay isused for studies with renin (A19). $C_3$-convertase is measured as described by Tack et al. (A20).

The individual assay references are elaborated upon by the following:

A1. The synthesis and analytical use of a highly sensitive and convenient substrate of elastase. J. Bieth, B. Spiess and C. G. Wermuth, *Biochemical Medicines,* 11 (1974) 350–375.

A2. Mapping the extended substrate binding site of cathepsin G and human leukocyte elastase. Studies with peptide substrates related to the alpha 1-protease inhibitor reactive site. K. Nakajima, J. C. Powers, B. M. Ashe and M. Zimmerman, *The Journal of Biological Chemistry,* 254 (1979) 4027–4032.

A3. Assay of coagulation proteases using peptide chromogenic and fluorogenic substrates. R. Lottenberg, U. Christensen, C. M. Jackson and P. L. Coleman, in, *Methods in Enzymology* (L. Lorand, ed), Academic Press, New York, 1979, vol. 80, pp. 341–361.

A4. Solution composition dependent variation in extinction coefficients for p-nitroaniline. R. Lottenberg and C. M. Jackson, *Biochimica et Biophysica Acta,* 742 (1983) 558–564.

A5. A rapid procedure for the large scale purifica-tion of elastase and cathepsin G from human sputum. R. R. Martodam, R. J. Baugh, D. Y. Twumasi and I. E. Liener, *Preparative Biochemistry,* 9 (1979) 15–31.

A6. The determination of enzyme inhibitor constants. M. Dixon, *The Biochemical Journal,* 55 (1953) 170–171.

A7. The kinetics of reversible tight-binding inhibition. J. W. Williams and J. F. Morrison, in, *Methodsin Enzymology* (D. L. Purich, ed), Academic Press, New York, 1979, vol. 63, pp. 437–467.

A8. Two convenient spectrophotometric enzyme assays.A biochemistry experiment in kinetics. J. A. Hurlbut, T. N. Ball, H. C. Pound and J. L. Graves, *Journal of Chemical Education,* 50 (1973) 149–151.

A9. The preparation and properties of two newchromogenic substrates of trypsin. B. F. Erlanger,N. Kokowsky and W. Cohen, *Archives of Biochemistry and Biophysics,* 95 (1961) 271–278.

A10. The human complement system serine proteases Clr and Cls and their proenzymes. R. B. Sim, in, Methods in *Enzymology* (L. Lorand, ed), Academic Press, New York, 1979,vol. 80, pp. 26–42.

A11. Extrinsic plasminogen activator and urokinase. J. H. Verheijen, C. Kluft, G. T. G. Chang and E. Mullaart, in, *Methods of Enzymatic Analysis* (H. U. Bergmeyer, J. Bergmeyer and M. Grassl, eds.), Verlag Chemie, Weinheim, 1984, third edition, vol. 5, pp. 425–433.

A12. Sperm acrosin. W. Mueller-Esterl and H. Fritz, in, *Methods in Enzymology* (L. Lorand, ed), Academic Press, New York, 1979, vol. 80, pp. 621–632.

A13. Novel method for detection of beta-lactamases by using a chromogenic cephalosporin substrate. C. H. O'Callaghan, A. Morris, S. M. Kirby and A. H. Shingler, *Antimicrobial Agents and Chemotherapy,* 1 (1972) 283–288.

A14. Cathepsin B, cathepsin H, and cathepsin L. A. J. Barrett and H. Kirschke, in, *Methods in Enzymology* (L. Lorand, ed), Academic Press, New York, 1979, vol. 80, pp. 535–561.

A15. Pepsins, gastricsins and their zymogens. A. P. Ryle, in, *Method of Enzymatic Analysis* (H. U. Bergmeyer, J. Bergmeyer and M. Grassl, eds), Verlag Chemie,Weinheim, 1984, third edition, vol. 5, pp. 223–238.

A16. Cathepsin D, cathepsin E. V. Turk, T. Lah and I. Kregar, in, *Methods of Enzymatic Analysis* (H. U. Bergmeyer, J. Bergmeyer and M. Grassl, eds), Verlag Chemie, Weinheim, 1984, third edition, vol. 5, pp. 211–222.

A17. Amino acid arylamidase. J. C. M. Hafkenscheid, in, Methods of Enzymatic Analysis (H. U. Bergmeyer, J. Bergmeyer and M. Grassl, eds), Verlag Chemie, Weinheim, 1984, third edition, vol. 5, pp. 11–15.

A18. Angiotensin I converting enzyme (kininase II). J. W. Ryan, in, *Methods of Enzymatic Analysis* (H. U. Bergmeyer, J. Bergmeyer and M. Grassl, eds), Verlag Chemie, Weinheim, 1984, third edition, vol. 5, pp. 20–34.

A19. Renin. T. Inagami and M. Naruse, in, *Methods of Enzymatic Analysis* (H. U. Bergmeyer, J. Bergmeyer and M. Grassl, eds), Verlag Chemie, Weinheim, 1984, third edition, vol. 5, pp. 249–258.

A20. The third, fourth, and fifth components of human complement: isolation and biochemical properties. B. F. Tack, J. Janatova, M. L. Thomas, R. A. Harrison and C. H. Hammer, in, *Methods in Enzymology* (L. Lorand, ed), Academic Press, New York, 1979, vol. 80, pp. 64–101.

By following the techniques referenced above, as well as by utilization of other known techniques, as well as by comparison with compounds known to be useful for treatment of the above-mentioned disease states, it is believed that adequate material is available to enable one of ordinary skill in the art to practice the invention. Of course, in the end-use application of the compounds of this invention,the compounds are preferably formulated into suitable pharmaceutical preparations such as tablets, capsules or elixers, for oral administration or in sterile solutions orsuspensions for parenteral administration. The compounds of this invention can be administered to patients (animals and human) in need of such treatment in a dosage range of 0.01–10 mg per kg of body weight per day. As stated above,the dose will vary depending on severity of disease, weight of patient and other factors which a person skilled in the art will recognize.

Typically the compounds described above are formulatedinto pharmaceutical compositions as discussed below.

About 10 to 500 mg of a compound or mixture of compounds of Formula I or a physiologically acceptable salt is compounded with a physiologically acceptable vehicle, carrier, excipient, binder, preservative, stabilizer, flavor, etc., in a unit dosage form as called for by accepted pharmaceutical practice. The amount of active substance inthese compositions or preparations is such that a suitable dosage in the range indicated is obtained.

Illustrative of the adjuvants which may be incorporated in tablets, capsules and the like are the following: a binder such as gum tragacanth, acacia, corn starch or gelatin; an excipient such as microcrystalline cellulose; adisintegrating agent such as corn starch, pregelatinized starch, alginic acid and the like; a lubricant such as magnesium stearate; a sweetening agent such as sucrose, lactose or saccharin; a flavoring agent such as peppermint,oil of wintergreen or cherry. When the dosage unit form is a capsule, it may contain in addition to materials of the above type, a liquid carrier such as fatty oil. Various other materials may be present as coatings or to otherwise modify the physical form of the dosage unit. For instance,tablets may be coated with shellac, sugar or both. A syrupor elixer may contain the active compound, sucrose as a sweetening agent, methyl and propyl parabens as preservatives, a dye and a flavoring such as cherry or orange flavor.

sterile compositions for injection can be formulated according to conventional pharmaceutical practice by dissolving or suspending the active substance in a vehicle such as water for injection, a naturally occurring vegetable oil like sesame oil, coconut oil, peanut oil, cottonseed oil, etc. or a synthetic fatty vehicle like ethyl oleate or the like. Buffers, preservatives, antioxidants and the like can be incorporated as required.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or cus-tomary practice within the art to which the invention pertains and as may be applied to the essential features hereinbefore set forth, and as follows in the scope of the appended claims.

We claim:

1. A compound of the formula

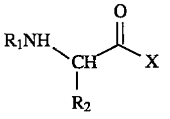

the hydrates thereof, and the pharmaceutically acceptable salts thereof useful for inhibiting human leukocyte elastase wherein $R_2$ is the side chain of the α-amino acids Ala, Leu, Ile, Val, n-Val or n-Leu, $R_1$ is $-P_2P_3P_4Pg$ with $P_2$ being Pro or Ala, $P_3$ is Ala, Leu, Ile, Val, n-Val, n-Leu or Lys, $P_4$ is Ala or is deleted, $P_g$ is an optional terminal moiety selected from Ac, Suc, Bz, Boc, CBZ, DNS, Iva, MeOSuc, $AdSO_2$, AcAc or 2-CBZ, X is $X_1$ or $X_2$ wherein $X_1$ is $-CF_3$, $-CF_2H$, -CO2R$_3$ or $-CONHR_3$, X2 is

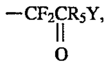

Y is $-OR_3$, $R_3$ is hydrogen, $C_{1-4}$ straight or branched alkyl, phenyl, benzyl, cyclohexyl or cyclohexylmethyl, and $R_5$ is deleted, with the proviso that when the $R_1$ moiety bears a Pro in its $P_2$ position, then X is other than $CF_3$.

2. A compound of the formula

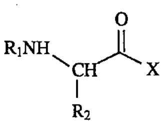

the hydrates thereof, and the pharmaceutically acceptable salts thereof useful for inhibiting Cathepsin G wherein X, $X_1$, $X_2$, $R_3$, $R_5$ and Y are as defined in claim 1.

$R_1$ is $-P_2P_3P_4Pg$ with $P_2$ being selected from Pro or Ala or is selected from Ac, Suc, Bz, Boc, CBZ, DNS, Iva, MeOSuc, $AdSO_2$, AcAc or 2-CBZ when $P_3$, $P_4$ and $P_g$ are deleted, $P_3$ is Ala, Leu, Ile, Val, n-Val, n-Leu, Gly, or is deleted, $P_4$ is Ala or is deleted, $P_g$ is selected from the group consisting of Ac, Suc, Bz, Boc, CBZ, DNS, Iva, MeOSuc, $AdSO_2$, AcAc or 2-CBZ or is deleted, and $R_2$ is a side chain of an amino acid selected from Phe or Tyr.

3. A compound of the formula

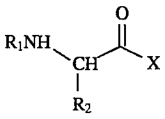

the hydrates thereof, and the pharmaceutically acceptable salts thereof useful for inhibiting chymotrypsin wherein X, $X_1$, $X_2$, $R_3$, $R_5$ and Y are as defined in claim 1, $R_1$ is $-P_2P_3P_4Pg$ with $P_2$ being selected from Ala, Val or n-Val or is selected from Ac, Suc, Bz, Boc, CBZ, DNS, Iva, MeOSuc, $AdSO_2$, AcAc or 2-CBZ when $P_3$, $P_4$ and $P_g$ are deleted, $P_3$ is deleted, $P_4$ is deleted, $P_g$ is selected from the group consisting of Ac, Suc, Bz, Boc, CBZ, DNS, Iva, MeOSuc, $AdSO_2$, AcAc or 2-CBZ or is deleted, and $R_2$ is a side chain of an amino acid selected from Phe or Tyr.

4. A compound of claim 1 having one of the formulae
MeOSuc-Ala-Ile-Pro-Val-$CO_2$Me,
MeOSuc-Ala-Ile-Pro-Val-$CF_2$COOEt,
MeOSuc-Ala-Ile-Pro-Val-$CHF_2$,
MeOSuc-Ala-Ala-Pro-Val-$CO_2$Me,
Lys-Pro-Val-$CHF_2$,
Lys-Pro-Val-$CO_2$Me, and
MeOSuc-Ala-Ile-Pro-Val-$CO_2$H.

5. A compound of claim 2 having one of the formulae
Suc-Ala-Ala-Pro-Phe-COOH,
Suc-Ala-Ala-Pro-Phe-COOMe,
Suc-Ala-Ala-Pro-Phe-$CF_2$H, and Suc-Ala-Ala-Pro-Phe-$CF_2COOEt$.

6. A compound of claim 3 having one of the formulae

Bz-Phe-$CF_3$,

Bz-Phe-COOH,

Bz-Phe-COOMe,

Bz-Tyr-$CF_3$,

Bz-Tyr-COOH,

Bz-Tyr-COOMe,

Bz-Phe-$CHF_2$, and

Bz -Phe-$CF_2COOEt$.

7. A compound of claim 4 having the formula MeOSuc-Ala-Ala-Pro-Val-$CO_2Me$.

* * * * *

UNITED STATES PATENT AND TRADEMARK OFFICE

CERTIFICATE OF CORRECTION

PATENT NO. : 5,496,927

DATED : March 5, 1996

INVENTOR(S) : Kolb, et al.

It is certified that error appears in the above-identified patent and that said Letters Patent is hereby corrected as shown below:

Column 4, Line 6 of Patent reads "$X_1$" and should read --X--.

Column 12, Line 33 of Patent reads "glomerulone-phritiso" and should read --glomerulonephritis--.

Column 32, Line 40 of Patent reads "Et20" and should read --$Et_2O$--.

Column 33, Line 61 of Patent reads "N1" and should read --$N^1$--.

Column 34, Line 36; Column 35, Line 41; Column 36, Line 2 and Column 36, Line 11 of the Patent reads "Tort" and should read --Torr--.

Column 50, Line 4 of Patent reads "$N_2$" and should read --$N^2$--.

Column 53, Line 67 of Patent reads "$CO2R_3$" and should read --$CO_2R_3$--.

Signed and Sealed this

Twenty-seventh Day of October, 1998

Attest:

BRUCE LEHMAN

*Attesting Officer* *Commissioner of Patents and Trademarks*